US008466171B2

(12) United States Patent
Shan et al.

(10) Patent No.: US 8,466,171 B2
(45) Date of Patent: Jun. 18, 2013

(54) FUSED HETEROCYCLIC COMPOUNDS USEFUL AS MODULATORS OF NUCLEAR HORMONE RECEPTOR FUNCTION

(75) Inventors: Weifang Shan, Princeton, NJ (US); James Aaron Balog, Lambertville, NJ (US); Ashvinikumar V. Gavai, Princeton Junction, NJ (US); Yufen Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 443 days.

(21) Appl. No.: 12/740,221

(22) PCT Filed: Oct. 31, 2008

(86) PCT No.: PCT/US2008/081903
§ 371 (c)(1),
(2), (4) Date: Apr. 28, 2010

(87) PCT Pub. No.: WO2009/059077
PCT Pub. Date: May 7, 2009

(65) Prior Publication Data
US 2010/0256180 A1    Oct. 7, 2010

Related U.S. Application Data

(60) Provisional application No. 60/984,441, filed on Nov. 1, 2007.

(51) Int. Cl.
*C07D 221/22* (2006.01)
*A61K 31/439* (2006.01)

(52) U.S. Cl.
USPC .............. 514/301; 514/302; 514/373; 546/97

(58) Field of Classification Search
USPC .................. 546/97; 548/207; 514/301, 302, 514/373
See application file for complete search history.

(56) References Cited

U.S. PATENT DOCUMENTS

| | | | |
|---|---|---|---|
| 5,296,496 | A | 3/1994 | Desai et al. |
| 6,670,386 | B2 | 12/2003 | Sun et al. |
| 6,960,474 | B2 | 11/2005 | Salvati et al. |
| 7,001,911 | B2 | 2/2006 | Salvati et al. |
| 7,087,636 | B2 | 8/2006 | Salvati et al. |
| 7,141,578 | B2 | 11/2006 | Salvati et al. |
| 7,235,563 | B2 | 6/2007 | Balog |
| 7,550,458 | B2 | 6/2009 | Balog et al. |
| 7,655,688 | B2 | 2/2010 | Salvati et al. |
| 2003/0181728 | A1 | 9/2003 | Salvati |
| 2005/0187267 | A1 | 8/2005 | Hamann et al. |
| 2005/0187273 | A1 | 8/2005 | Salvati et al. |
| 2005/0197367 | A1 | 9/2005 | Li et al. |
| 2006/0111424 | A1 | 5/2006 | Salvati et al. |
| 2007/0088039 | A1 | 4/2007 | Balog et al. |

FOREIGN PATENT DOCUMENTS

| | | |
|---|---|---|
| EP | 0220051 | 4/1987 |
| WO | WO 03/053358 | 7/2003 |
| WO | WO 2008/030902 | 3/2008 |
| WO | WO 2009/003077 | 12/2008 |

OTHER PUBLICATIONS

Dorwald F. A. Side Reactions in Organic Synthesis, 2005, Wiley: VCH, Weinheim p. IX of Preface.*
Beer, R. J. S., et al., "Studies on 5-Benzoyl-3-Isothiazolinones", Tetrahedron, vol. 37(22), pp. 3867-3870 (1981).
Harned, A. M., et al., "Ring-Opening Metathesis Phase-Trafficking (ROMpt) Synthesis: Multistep Synthesis on Soluble ROM Supports", Organic Letters, vol. 5(1), pp. 15-18 (2003).
Ho, K. F., et al., "Synthesis and Diels-Alder reactions of α,β-unsaturated-γ-sultams", Tetrahedron Letters, vol. 42, pp. 3121-3124 (2001).
Jiang L-S., et al., "Synthesis and Diels-Alder Reactions of Prop-1-ene-1,3- sultone, and Chemical Transformations of the Diels-Alder Adducts", Tetrahedron, vol. 55, pp. 2245-2262 (1999).
Lee, A. W. M., et al., "Ruthenium catalyzed asymmetric dihydroxylation with sultams as chiral auxiliaries", Tetrahedron: Asymmetry, vol. 10, pp. 1421-1424 (1999).
Lee, A. W. M., et al., "Synthesis and Diels-Alder reactions of α,β-unsaturated γ-sultone", Chem. Commun., vol. 6, pp. 611-612 (1997).
Lin, J., et al., "Asymmetric synthesis of 1,3- and 1,3,4-substituted pyrrolidines", Tetrahedron Letters, vol. 41, pp. 2949-2951 (2000).
Lin, J., et al., "Asymmetric Alkylation Mediated by Tricyclic Chiral Sultam Auxiliaries", Tetrahedron, vol. 55, 13983-13998 (1999).
Wanner, J., et al., "A dual metathesis route to oligomeric sulfonamides", Tetrahedron Letters, vol. 43, pp. 917-921 (2002).
Beilstein Abstract, BRN: 5129935, Aug. 28, 1992.
Beilstein Abstract, BRN: 9335197, Jul. 25, 2003.
Beilstein Abstract, BRN: 9350372, Jul. 25, 2003.
Beilstein Abstract, BRN: 9359394, Jul. 25, 2003.
Beilstein Abstract, BRN: 9362313, Jul. 25, 2003.
Beilstein Abstract, BRN: 9364304, Jul. 25, 2003.
Beilstein Abstract, BRN: 9366506, Jul. 25, 2003.
Beilstein Abstract, BRN: 9367324, Jul. 25, 2003.
Beilstein Abstract, BRN: 9368944, Jul. 25, 2003.
Beilstein Abstract, BRN: 9369766, Jul. 25, 2003.
Beilstein Abstract, BRN: 9371255, Jul. 25, 2003.

\* cited by examiner

*Primary Examiner* — Rita Desai
(74) *Attorney, Agent, or Firm* — Burton Rodney; Gary D. Greenblatt

(57) ABSTRACT

Disclosed are fused heterocyclic compounds of Formula (I):

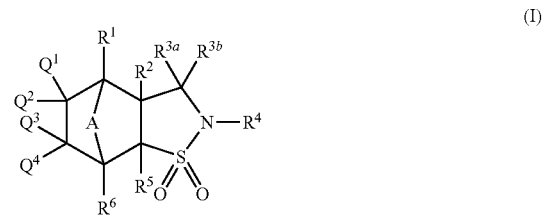

or pharmaceutically-acceptable salts or stereoisomers thereof. Also disclosed are methods of using such compounds in the treatment of at least one androgen receptor-associated condition, such as, for example, cancer, and pharmaceutical compositions comprising such compounds.

3 Claims, No Drawings

FUSED HETEROCYCLIC COMPOUNDS USEFUL AS MODULATORS OF NUCLEAR HORMONE RECEPTOR FUNCTION

FIELD OF THE INVENTION

The present invention generally relates to fused heterocyclic compounds, to methods of using such compounds in the treatment of androgen receptor-associated conditions such as cancer, and to pharmaceutical compositions comprising the compounds.

BACKGROUND OF THE INVENTION

Carcinoma of the prostate (CaP) is the second leading cause of cancer-related death in men. Reportedly, there were an estimated 221,000 new cases of CaP diagnosed in 2003 with an estimated 28,900 deaths. See American Cancer Society, *Key Statistics about Prostate Cancer* 2003; Jemal et al., *CA Cancer J. Clin.*, 52:23-47 (2002). CaP presents a relatively high rate of morbidity and mortality necessitating prompt detection and effective treatment.

CaP has been commonly treated with surgery, i.e., radical prostatectomy. This procedure presents drawbacks in terms of surgical risks and impairment, and additionally, its usefulness may be limited to early-stage, organ-confined cancers. In advanced cases, the cancer may have spread beyond the bounds of the removed tissue, making it unlikely surgery will be a successful treatment. Radiation therapy also has been widely used as an alternative and/or supplement to surgery but with limited success.

In recent years, various treatment strategies have focused on inhibiting the role of androgens [testosterone (T) and dihydrotestosterone (DHT)] in prostate tumor growth. The androgen receptor (AR) is a ligand-binding transcription factor in the nuclear-hormone receptor (NHR) superfamily, and it is an important mediator of prostate cancer development and growth. The androgens (T and DHT) compete for binding to the AR (DHT having a higher binding affinity than T), and both T and DHT activate the AR, influencing cell function and stimulating growth of the prostate and other tissue, including prostate tumor cells.

Recent efforts for treating CaP have focused on developing compounds that act as androgen receptor modulators. A compound that binds to the AR and mimics the effect of the natural ligand (e.g., T or DHT) is referred to as an "agonist", while a compound that inhibits the effect of a natural ligand in binding to the AR is referred to as an "antagonist". AR antagonist and/or agonists (collectively "antiandrogens") have proven useful in the treatment of CaP.

However, AR is related to other members of the subfamily of NHR's, which share a sequence homology to one another. Other members of this sub-family include the estrogen receptor (ER), the progesterone receptor (PR), the glucocorticoid receptor (GR), the mineralcorticoid receptor (MR), and the aldosterone receptor (ALDR). Ligands to these receptors are known to play an important role in the health of men and women. Given the similarity in sequence homology of these NHR's, the development of compounds which have good specificity for one or more steroid receptors, but which have reduced or no cross-reactivity for other steroid receptors (thus reducing or avoiding undesirable side effects), has presented challenges. There are several known, approved non-steroidal antiandrogens including bicalutamide, Eulexin, and Anandrone. However, these antiandrogens may bind reversibly to the AR, and if treatment is continued for a period of years, tumors may become androgen independent. Androgen-independent tumors are not affected by the natural ligands (T and DHT), and thus, antiandrogens may lose effectiveness in treating androgen-independent tumors.

As may be appreciated, there remains a need for more potent AR antagonists and/or AR antagonist with a different pharmacological profile as compared with currently-known antiandrogens.

SUMMARY OF THE INVENTION

Described herein are compounds of Formula (I):

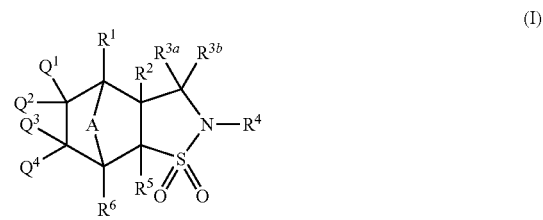

or pharmaceutically-acceptable salts or stereoisomers thereof, wherein:

A is —O—, —CR$^{7a}$R$^{7b}$O—, —OCR$^{7a}$R$^{7b}$—, —NR$^8$—, —C(=O)NR$^8$—, —NR$^8$C(=O)—, —CR$^{7a}$R$^{7b}$NR$^8$—, or —NR$^8$CR$^{7a}$R$^{7b}$—;

R$^1$ and R$^6$ are independently H, alkyl, substituted alkyl, alkenyl, substituted alkenyl, alkynyl, and/or substituted alkynyl;

R$^2$ is H, alkyl, substituted alkyl, alkenyl, substituted alkenyl, alkynyl, or substituted alkynyl;

R$^{3a}$ and R$^{3b}$ are independently H, alkyl, substituted alkyl, alkenyl, substituted alkenyl, alkynyl, and/or substituted alkynyl;

R$^4$ is aryl, substituted aryl, heteroaryl, or substituted heteroaryl, wherein R$^4$ is attached to the N atom of the core rings via a carbon atom of R$^4$;

R$^5$ is H, alkyl, substituted alkyl, alkenyl, substituted alkenyl, alkynyl, substituted alkynyl, —C(=O)R$^b$, —C(=O)NR$^b$R$^c$, or —C(=O)OR$^a$;

R$^{7a}$ and R$^{7b}$ are independently H, alkyl, substituted alkyl, cycloalkyl, substituted cycloalkyl, and/or CN; or R$^{7a}$ and R$^{7b}$ together with the carbon atom to which they are attached form a cycloalkyl ring;

R$^8$ is H, alkyl, substituted alkyl, alkenyl, substituted alkenyl, alkynyl, substituted alkynyl, —C(=O)R$^b$, —C(=O)NR$^b$R$^c$, —C(=O)OR$^a$, or —SO$_2$R$^a$;

Q$^1$, Q$^2$, Q$^3$, and Q$^4$ are independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxyamide, thiol, alkylthio, substituted alkylthio, halo, CN, —C(=O)R$^b$, —C(=O)NR$^b$R$^c$, —C(=O)OR$^a$, —NR$^b$R$^c$, —NR$^b$OR$^a$, —NR$^a$C(=O)R$^a$, —NR$^a$C(=O)NR$^b$R$^c$, —NR$^a$C(=O)OR$^a$, —NR$^a$SO$_2$R$^a$, —NR$^a$SO$_2$NR$^b$R$^c$, N$_3$, NO$_2$, —OR$^a$, —OC(=O)R$^b$, —OC(=O)NR$^b$R$^c$, —SO$_2$R$^a$, —SO$_2$NR$^b$R$^c$, and/or —SO$_2$OR$^a$; or Q$^1$ and Q$^2$ together form =CR$^d$R$^d$, =O, =NR$^d$, =NOR$^b$, or =NNR$^c$R$^d$; and/or Q$^3$ and Q$^4$ together form =CR$^d$R$^d$, =O, =NR$^d$, =NOR$^b$, or =NNR$^c$R$^d$; or Q$^1$ and Q$^3$ together form —O—, —CR$^d$R$^d$—, —NR$^b$—, or a carbon-carbon bond, and Q$^2$ and Q$^4$ are independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$;

each R$^a$ is independently H, alkyl, substituted alkyl, aryl, substituted aryl, heterocyclo, and/or substituted heterocyclo;

each R$^b$ is independently H, alkyl, substituted alkyl, aryl, substituted aryl, heterocyclo, and/or substituted heterocyclo;

each R$^c$ is independently H, alkyl, substituted alkyl, aryl, substituted aryl, heterocyclo, and/or substituted heterocyclo; or R$^b$ and R$^c$ together with the nitrogen atom to which they are attached form a 4-7 membered heterocyclo or substituted heterocyclo ring; and each R$^d$ is independently H, —C(=O)OR$^a$, —C(=O)NR$^b$R$^c$, —OR$^a$, —SO$_2$R$^a$, —SO$_2$NR$^b$R$^c$, alkyl, substituted alkyl, aryl, substituted aryl, heterocyclo, and/or substituted heterocyclo, and/or substituted heterocyclo.

Further described herein is at least one pharmaceutical composition comprising at least one compound of Formula (I) or a pharmaceutically-acceptable salt or stereoisomer thereof; and at least one pharmaceutically acceptable carrier and/or diluent.

Even further described herein is a method of modulating the function of at least one nuclear hormone receptor comprising administering to a patient in need thereof, an effective amount of at least one compound of Formula (I), or a pharmaceutically-acceptable salt or stereoisomer thereof.

Yet even further described herein is at least one method of treating a condition or disorder comprising administering to a mammalian species in need thereof a therapeutically effective amount of at least one compound of Formula (I) or a pharmaceutically-acceptable salt or stereoisomer thereof.

DETAILED DESCRIPTION OF THE INVENTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group. Throughout the specification, groups and substituents thereof may be chosen by one skilled in the field to provide stable moieties and compounds.

The terms "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl; ethyl; propyl; isopropyl; n-butyl, isobutyl; t-butyl; pentyl; hexyl; isohexyl; heptyl; 4,4-dimethylpentyl; dimethylpentyl; octyl; 2,2,4-trimethylpentyl; nonyl; decyl; undecyl; and dodecyl.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "$C_{0-4}$alkyl" includes a bond and an alkyl group containing 1 to 4 carbon atoms, and the term "$C_{1-4}$alkyl" refers to alkyl groups containing 1 to 4 carbon atoms. Exemplary lower alkyl groups include, but are not limited to, for example, methyl; ethyl; propyl; isopropyl; n-butyl; t-butyl; and isobutyl.

The term "substituted alkyl" refers to an alkyl group substituted with at least one substituent, preferably 1 to 4 substituents, at any available and substitutable position. Exemplary substituents include, but are not limited to, for example, halo (e.g., a single halo substituent or multiple halo substituents forming, in the latter case, groups such as, for example, a perfluoroalkyl group or an alkyl group bearing —CCl$_3$ or —CF$_3$); alkoxy; alkylthio; hydroxyl; carboxy (i.e., —COOH); alkoxycarbonyl; alkylcarbonyloxy; CN; amino (i.e., —NH$_2$); alkylamino; dialkylamino; carbamoyl; carbamate; urea; amidinyl; thiol (i.e., —SH); heterocycle; cycloalkyl; heterocycloalkyl; —S-aryl; —S-heterocycle; —S(=O)-aryl; —S(=O)-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-aryl; —NHS(O)$_2$NH-heterocycle; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)—heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)O-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)— heterocycle; —N(alkyl)C(=O)NH-aryl; N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; and —Si(alkyl)$_3$. In the aforementioned exemplary substituents, in each instance, groups such as "alkyl" and "cycloalkyl" can themselves be substituted with groups selected from —CF$_3$, halogen, —C≡CH, —CN, —NH$_2$, —OCF$_3$, and —NO$_2$. In the aforementioned exemplary substituents, in each instance, groups such as "aryl", and "heterocycle" can themselves be substituted with groups selected from methyl, cyclopropyl, —CF$_3$, halogen, —C≡CH, —CN, —NH$_2$, —OCF$_3$, and —NO$_2$.

The term "substituted lower alkyl" refers to a lower alkyl substituted at any available and substitutable position with at least one substituent described above in defining the term "substituted alkyl" as an exemplary alkyl substituent.

The term "aryl" refers to cyclic aromatic hydrocarbon groups having from 1 to 3 aromatic rings, especially monocyclic or bicyclic groups, such as, for example, phenyl, biphenyl, or naphthyl. When the aryl group contains two or more aromatic rings (e.g., bicyclic, etc.), the aromatic rings may be joined at a single point (e.g., biphenyl) or fused (e.g., naphthyl and phenanthrenyl).

The term "substituted aryl" refers to an aryl substituted with at least one substituent, preferably 1 to 5 substituents, at any available and substitutable ring position, or where valence allows on any rings fused or attached thereto. Exemplary substituents include, but are not limited to, for example, alkyl, substituted alkyl, or those recited hereinabove for substituted alkyl.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl. The term "substituted alkenyl" refers to an alkenyl substituted with at least one substituent, preferably 1 to 4 substituents, at any available point of attachment. Exemplary substituents include, but are not limited to, for example, substituted alkyl; alkenyl; and the substituents recited above in defining the term "substituted alkyl" as exemplary alkyl substituents.

The term "cycloalkyl" refers to a fully saturated hydrocarbon group containing from 1 to 4 rings and 3 to 8 carbons per ring. Exemplary cycloalkyl groups include, but are not limited to, for example, cyclopropyl, cyclobutyl, cyclopentyl, cyclohexyl, and cycloheptyl.

The term "substituted cycloalkyl" refers to a cycloalkyl substituted with at least one substituent, preferably 1 to 4 substituents, at any available point of attachment. Exemplary substituents include groups those recited for substituted alkyl.

The term "cycloalkenyl" refers to a partially saturated hydrocarbon group having at least one double bond in the ring and containing from 1 to 4 rings and 3 to 8 carbons per ring. Exemplary cycloalkenyl groups include, but are not limited to, for example, cyclobutenyl, cyclopentenyl, and cyclohexenyl.

The term "substituted cycloalkenyl" refers to a cycloalkenyl substituted with at least one substituent, preferably 1 to 4 substituents, at any available point of attachment. Exemplary substituents include, but are not limited to, for example, the substituents described above in defining the term "substituted alkenyl" as exemplary alkenyl substituents.

The term "alkylamino" refers to an amino group having one hydrogen atom replaced with an alkyl. Thus, alkylamino refers to the group —NH(alkyl).

The term "substituted alkylamino" refers to an alkylamino group having one hydrogen atom is replaced with a substituted alkyl. Thus, alkylamino refers to the group —NH(substituted alkyl).

The term "dialkylamino" refers to an amino group having both of the hydrogen atoms replaced with a group chosen from alkyl and/or substituted alkyl.

The terms "alkoxy" or "alkylthio" refers to an alkyl bonded through an oxygen linkage (—O—) or a sulfur linkage (—S—), respectively.

The terms "substituted alkoxy" or "substituted alkylthio" refer to a substituted alkyl bonded through an oxygen or sulfur linkage, respectively.

The term "carbonyl" refers to C(=O).

The term "alkoxycarbonyl" refers to an alkoxy bonded through a carbonyl. Thus, alkoxycarbonyl refers to the group —C(=O)O(alkyl).

The term "alkylcarbonyl" refers to an alkyl bonded through a carbonyl. Thus, alkylcarbonyl refers to the group —C(=O)(alkyl).

The term "alkylcarbonyloxy" refers to an alkylcarbonyl bonded through an oxygen linkage. Thus, alkylcarbonyloxy refers to the group —OC(=O)(alkyl).

The terms "heterocycle", heterocyclic" and "heterocyclo" refer to fully saturated, partially saturated, or fully unsaturated, aromatic (i.e., "heteroaryl") or nonaromatic cyclic groups that are, for example, 3 to 7 membered monocyclic, 7 to 11 membered bicyclic, or 10 to 16 membered tricyclic ring systems having at least one heteroatom in at least one carbon atom-containing ring. Each ring of the heterocycle, heterocyclic, or heterocyclo containing a heteroatom may have 1, 2, 3, or 4 heteroatoms selected from N, O, and/or S, where the N and/or S heteroatom(s) may optionally be oxidized and the N heteroatom(s) may optionally be quaternized. A heterocycle, heterocyclic, or heterocyclo may be attached to the remainder of the molecule at any heteroatom or carbon atom of the ring or ring system.

Exemplary groups containing a quaternized N include, but are not limited to, for example, a tetraalkylammonium group, such as, for example, tetramethylammonium and N-methylpyridinium; a protonated ammonium species, such as, for example, trimethylhydroammonium and N-hydropyridinium; an amine N-oxide, such as, for example, N-methylmorpholine-N-oxide and pyridine-N-oxide; and an N-aminoammonium group, such as, for example, N-aminopyridinium.

Exemplary monocyclic heterocycles, heterocyclics, or heterocyclos include, but are not limited to, for example, ethylene oxide; azetidinyl; pyrrolidinyl; pyrrolyl; pyrazolyl; oxetanyl; pyrazolinyl; imidazolyl; imidazolinyl; imidazolidinyl; oxazolyl; oxazolidinyl; isoxazolinyl; isoxazolyl; thiazolyl; thiadiazolyl; thiazolidinyl; isothiazolyl; isothiazolidinyl; furyl; tetrahydrofuryl; thienyl; oxadiazolyl; piperidinyl; piperazinyl; 2-oxopiperazinyl; 2-oxopiperidinyl; 2-oxopyrrolidinyl; 2-oxoazepinyl; azepinyl; hexahydrodiazepinyl; 4-piperidonyl; pyridyl; pyrazinyl; pyrimidinyl; pyridazinyl; triazinyl; triazolyl; tetrazolyl; tetrahydropyranyl; morpholinyl; thiamorpholinyl; thiamorpholinyl sulfoxide; thiamorpholinyl sulfone; 1,3-dioxolane; and tetrahydro-1,1-dioxothienyl.

Exemplary bicyclic heterocycles, heterocyclics, or heterocyclos include, but are not limited to, for example, indolyl; isoindolyl; benzothiazolyl; benzodioxolyl; benzoxazolyl; benzoxadiazolyl; benzothienyl; quinuclidinyl; quinolinyl; tetrahydroisoquinolinyl; isoquinolinyl; benzimidazolyl; benzopyranyl; indolizinyl; benzofuryl; benzofurazanyl; chromonyl; coumarinyl; benzopyranyl; cinnolinyl; quinoxalinyl; indazolyl; pyrrolopyridyl; furopyridinyl, such as, for example, furo[2,3-c]pyridinyl, furo[3,2-b]pyridinyl], and furo[2,3-b]pyridinyl; dihydrobenzodioxinyl; dihydrodioxidobenzothiophenyl; dihydroisoindolyl; dihydroindolyl; dihydroquinolinyl; dihydroquinazolinyl, such as, for example, 3,4-dihydro-4-oxo-quinazolinyl; triazinylazepinyl; and tetrahydroquinolinyl.

Exemplary tricyclic heterocycles, heterocyclics, or heterocyclos include, but are not limited to, for example, carbazolyl; benzidolyl; phenanthrolinyl; dibenzofuranyl; acridinyl; phenanthridinyl; and xanthenyl.

The terms "substituted heterocycle," "substituted heterocyclic," and "substituted heterocyclo" refer to a heterocycle, heterocyclic, or heterocyclo substituted at any available point of attachment with at least one substituent, preferably 1 to 4 substituents, selected from alkyl and those recited for substituted alkyl.

The term "heteroaryl" refers to an aromatic heterocycle, heterocyclic, or heterocyclo.

The term "substituted heteroaryl" refers to an aromatic heterocycle, heterocyclic, or heterocyclo substituted with at least one substituent, preferably 1 to 4 substituents, at any available point of attachment. Exemplary substituents include, but are not limited to, for example, the substituents describe above in defining the terms "substituted heterocycle," "substituted heterocyclic," and "substituted heterocyclo".

The term "nitro" refers to the group —$NO_2$.

The term "carbamoyl" refers to the group —C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "carbamate" refers to the group —O—C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "urea" refers to the group —NH—C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "amidinyl" refers to the group —C(=NH)($NH_2$).

The terms "substituted carbamoyl", "substituted carbamate", "substituted urea", and "substituted amidinyl" refer to a carbamoyl, carbamate, urea, and amidinyl, respectively, in which one more hydrogen group is replaced by an organic moiety, such as, for example, alkyl, substituted alkyl, aryl, substituted aryl, heterocycle, alkylcarbonyl, hydroxyl, and substituted nitrogen.

The terms "halogen" and "halo" refer to fluorine, chlorine, bromine, and iodine.

The term "salt(s)", as employed herein, denotes acidic and/or basic salts formed with inorganic and/or organic acids and/or bases, and such term, as used herein, further includes zwitterion(s) ("inner salts").

The terms "zwitterion(s)", as employed herein, denote compound(s) containing both a basic moiety, including but not limited to, for example, amine, pyridine and imidazole; and an acidic moiety including but not limited to, for example, a carboxylic acid.

The term "pharmaceutically acceptable", as employed herein, indicates the subject matter being identified as "pharmaceutically acceptable" is suitable and physiologically acceptable for administration to a patient. For example, the term "pharmaceutically acceptable salt(s)" denotes suitable and physiologically acceptable salt(s).

When a functional group is termed "protected", the functional group is in a modified form to mitigate, especially to preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991). The compounds of Formula (I) can also form salts. As a result, when a compound of Formula (I) is referred to herein, such reference includes, unless otherwise indicated, salts thereof. In one embodiment, the compounds of Formula (I) form pharmaceutically acceptable salts. In another embodiment, the compounds of Formula (I) form salts that can, for example, be used to isolate and/or purify the compounds of Formula (I). Salt(s) of the Formula (I) compounds can be formed by, for example, reacting a Formula (I) compound with, for example, an equivalent amount of acid or base in a medium that allows the thusly formed salt to, for example, either be precipitated out, or be isolated via lyophilization.

Exemplary acidic salt(s) that the compounds of Formula (I) can form with inorganic and/or organic acids include, but are not limited to, for example, include acetates, ascorbates, benzoates, benzenesulfonates, bisulfates, citrates, sulfates, hydrochlorides, hydrobromides, hydroiodides, maleates, methanesulfonates, nitrates, salicylates, succinates, tartrates, p-toluenesulfonates, and lactates. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl)ethylenediamine), N-methyl-D-glucamines, N-methyl-D-glucamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

Prodrugs and solvates of the compounds of Formula (I) are also contemplated herein. The term "prodrug(s)", as employed herein, denotes a compound that, upon administration to a subject, undergoes chemical conversion via metabolic and/or chemical processes in vivo to yield a compound and/or derivative of Formula (I), or a salt and/or solvate thereof. Various forms of prodrug(s) are well known in the art. For examples of such prodrug derivatives, see:

a) *Design of Prodrugs*, edited by H. Bundgaard, (Elsevier, 1985) and *Methods in Enzymology*, 112:309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8:1-38 (1992).

The term "solvate", as employed herein, denotes a compound produced by the chemical interaction of at least one solvent with at least one solute comprising at least one compound of Formula (I). Exemplary solvates include, but are not limited to, for example, hydrates.

All stereoisomers and geometric isomer(s) of the compounds of Formula (I), such as, for example, stereoisomer(s) that exist due to asymmetric carbons on various substituents, either in a mixture or in pure or substantially pure form are further contemplated herein. In one embodiment, all enantiomers, tautomers, and diastereomers of the compounds of Formula (I), as well as mixtures, compounds, racemic compounds, racemic mixtures, and racemates produced therefrom are contemplated herein. In another embodiment, all optically active isomers of the compounds of Formula (I), including pure or substantially pure optically active isomers, i.e., optically active isomers substantially free of other isomers are contemplated herein.

When a compound containing a single enantiomer of a compound of Formula (I) is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of the compounds in accordance with Formula (I) can have the S or R configuration as defined by the IUPAC 1974 Recommendations.

In one embodiment, the compounds of Formula (I) are provided wherein:

A is —O—, —NR$^8$—, —C(=O)NR$^8$—, —NR$^8$C(=O)—, —CR$^{7a}$R$^{7b}$NR$^8$—, or —NR$^8$CR$^{7a}$R$^{7b}$—;

R$^1$ and R$^6$ are independently H, alkyl, and/or substituted alkyl;

R$^2$ is H, alkyl, or substituted alkyl;

R$^{3a}$ and R$^{3b}$ are independently H, alkyl, and/or substituted alkyl;

R$^4$ is substituted aryl or substituted heteroaryl;

R$^5$ is H, alkyl, substituted alkyl, —C(=O)R$^b$, —C(=O)NR$^b$R$^c$, or —C(=O)OR$^a$;

R$^{7a}$ and R$^{7b}$ are independently H, alkyl, substituted alkyl, and/or CN;

R$^8$ is H, alkyl, substituted alkyl, halo, N$_3$, —OR$^a$, —C(=O)R$^b$, —C(=O)NR$^b$R$^c$, —C(=O)OR$^a$, —NR$^b$R$^c$, or —SO$_2$R$^a$;

Q$^1$, Q$^2$, Q$^3$, and Q$^4$ are independently H, alkyl, substituted alkyl, hydroxylamide, halo, CN, —C(=O)R$^b$, —C(=O)NR$^b$R$^c$, —C(=O)OR$^a$, —NR$^b$R$^c$, —NR$^b$OR$^a$, —NR$^a$C(=O)R$^a$, —NR$^a$C(=O)NR$^b$R$^c$, —NR$^a$C(=O)OR$^a$, —NR$^a$SO$_2$R$^a$, —NR$^a$SO$_2$NR$^b$R$^c$, N$_3$, NO$_2$, —OR$^a$, —OC(=O)R$^b$, —OC(=O)NR$^b$R$^c$, —SO$_2$R$^a$, —SO$_2$NR$^b$R$^c$, and/or —SO$_2$OR$^a$; or Q$^1$ and Q$^3$ together form —O—, CR$^d$R$^d$, or a carbon-carbon bond, and Q$^2$ and Q$^4$ are independently H, alkyl, substituted alkyl, hydroxylamine, CN, —C(=O)R$^b$, —C(=O)NR$^b$R$^c$, and/or —C(=O)OR$^a$;

each R$^a$ is independently H, C$_{1-4}$alkyl, substituted C$_{1-4}$alkyl, aryl, substituted aryl, heterocyclo, and/or substituted heterocyclo;

each R$^b$ is independently H, C$_{1-4}$alkyl, substituted C$_{1-4}$alkyl, aryl, substituted aryl, heterocyclo, and/or substituted heterocyclo;

each R$^c$ is independently H, C$_{1-4}$alkyl, substituted C$_{1-4}$alkyl, aryl, substituted aryl, heterocyclo, and/or substituted heterocyclo; or R$^b$ and R$^c$ together with the nitrogen atom to which they are attached, can form a 4-7 membered heterocyclo or substituted heterocyclo ring; and each R$^d$ is independently H, —C(=O)OR$^a$, —C(=O)NR$^b$R$^c$, —OR$^a$, —SO$_2$R$^a$, —SO$_2$NR$^b$R$^c$, C$_{1-4}$alkyl, substituted C$_{1-4}$alkyl, aryl, substituted aryl, heterocyclo, and/or substituted heterocyclo, and/or substituted heterocyclo;

or pharmaceutically-acceptable salts or stereoisomers thereof.

In another embodiment, compounds of Formula (I) are provided wherein:

A is —O—, —NR$^8$—, —CR$^{7a}$R$^{7b}$NR$^8$—, or —NR$^8$CR$^{7a}$R$^{7b}$—;

R$^1$ is H or C$_{1-4}$alkyl;

R$^2$ is H or methyl;

R$^{3a}$ and R$^{3b}$ are independently H, C$_{1-4}$alkyl, and/or OH;

R$^4$ is aryl or pyridyl substituted with one or more of methyl, CF$_3$, CN, F, Cl, Br, I, —OCH$_3$, or —OCF$_3$;

R$^5$ is H, C$_{1-4}$alkyl, —C(=O)R$^b$, —C(=O)NHR$^c$, or —C(=O)OR$^a$;

R$^6$ is H or C$_{1-4}$alkyl;

R$^{7a}$ and R$^{7b}$ are independently H and/or C$_{1-4}$alkyl;

R$^8$ is H, —C(=O)R$^b$, —C(=O)OR$^a$, or —SO$_2$R$^a$; and

Q$^1$, Q$^2$, Q$^3$, and Q$^4$ are independently H, OH, halo, N$_3$, —NH$_2$, C$_{1-4}$alkyl, —NHSO$_2$R$^a$, and/or NR$^a$C(=O)OR$^a$; or Q$^1$ and Q$^3$ together form —O— or a carbon-carbon bond;

or pharmaceutically-acceptable salts or stereoisomers thereof.

In one embodiment, compounds of Formula (I) are provided wherein:

A is —O—, —NR$^8$CH$_2$—, or —CH$_2$NR$^8$—;

R$^1$ is H or methyl;

R$^2$ is H;

R$^{3a}$ and R$^{3b}$ are each H;

R$^4$ is

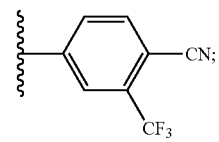

R$^5$ is H, —C(=O)OR$^a$ wherein R$^a$ is H or methyl substituted with phenyl, or —C(=O)NH—CH$_3$;

R$^6$ is H or methyl;

R$^{7a}$ and R$^{7b}$ are each H;

R$^8$ is H, —C(=O)R$^b$ wherein R$^b$ is methyl, —C(=O)OR$^a$ wherein R$^a$ is phenyl or methyl substituted with phenyl, or —SO$_2$R$^a$ wherein R$^a$ is ethyl; and Q$^1$, Q$^2$, Q$^3$, and Q$^4$ are independently H, OH, F, N$_3$, —NH$_2$, and/or —NHC(=O)OCH$_3$; or Q$^1$ and Q$^3$ together form —O— or a carbon-carbon bond;

or pharmaceutically-acceptable salts or stereoisomers thereof.

In one embodiment, compounds of Formula (I) or pharmaceutically-acceptable salts or stereoisomers thereof, are provided wherein R$^4$ is a substituted aryl or substituted heteroaryl having, for example, from 1 to 3 substituents. Preferably, R$^4$ is a substituted aryl having one or two rings.

In a further embodiment, compounds of Formula (I) or pharmaceutically-acceptable salts or stereoisomers thereof, are provided wherein R$^4$ is substituted phenyl, substituted naphthyl, substituted pyridyl, substituted quinoline, substituted isoquinoline, or substituted benzoxadiazol. In this embodiment, R$^4$ may be substituted with 1, 2, or 3 substituents. Preferably, the optional 1, 2, or 3 substituents are each independently —CN, Cl, Br, I, CF$_3$, methyl, and/or —OR$^e$, wherein R$^e$ is lower alkyl or substituted lower alkyl.

Examples of suitable R$^4$ groups include, but are not limited to:

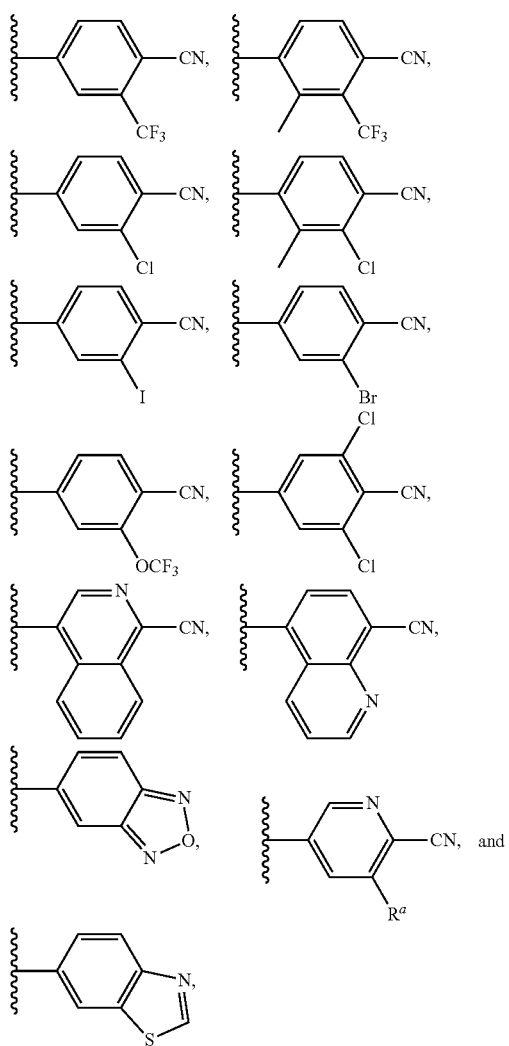

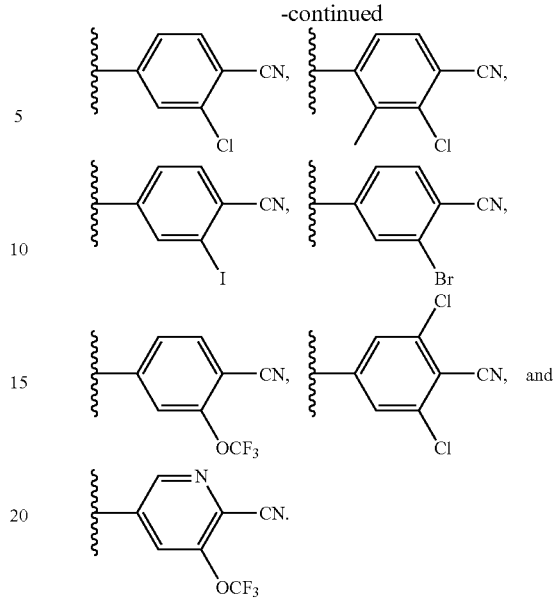

wherein $R^a$ is alkyl, substituted alkyl, or —$OR^e$; and $R^e$ is alkyl or substituted alkyl.

According to another embodiment, compounds of Formula (I) or pharmaceutically-acceptable salts or stereoisomers thereof, are provided wherein $R^4$ is a phenyl substituted at the 4-position, and optionally substituted at the 2- and/or 3-positions.

In one embodiment, compounds of Formula (I) or pharmaceutically-acceptable salts or stereoisomers thereof, are provided wherein $R^4$ is phenyl substituted with at least one of CN, Cl, Br, I, $CF_3$, methyl, and/or —$OR^{11}$; and $R^{11}$ is lower alkyl or substituted lower alkyl.

In a further embodiment, compounds of Formula (I) or pharmaceutically-acceptable salts or stereoisomers thereof, are provided wherein $R^4$ is a cyano substituted phenyl or pyridyl. Examples of suitable cyano substituted phenyl and pyridyl groups include:

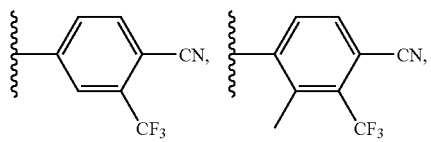

In one embodiment, compounds of Formula (I) or pharmaceutically-acceptable salts or stereoisomers thereof, are provided wherein at least two of $Q^1$, $Q^2$, $Q^3$, and $Q^4$ are H. The present embodiment includes compounds of Formula (I) wherein at least three of $Q^1$, $Q^2$, $Q^3$, and $Q^4$ are H; and compounds of Formula (I) wherein each of $Q^1$, $Q^2$, $Q^3$, and $Q^4$ are H.

In one embodiment, compounds of Formula (I) or pharmaceutically-acceptable salts or stereoisomers thereof, are provided wherein $Q^1$, $Q^2$, $Q^3$, and $Q^4$ are independently H, alkyl, substituted alkyl, hydroxylamide, halo, CN, —C(=O)$R^b$, —C(=O)$NR^bR^c$, —C(=O)$OR^a$, —$NR^bR^c$, —$NR^bOR^a$, —$NR^aC$(=O)$R^a$, —$NR^aC$(=O)$NR^bR^c$, —$NR^aC$(=O)$OR^a$, —$NR^aSO_2R^a$, —$NR^aSO_2NR^bR^c$, $N_3$, $NO_2$, —$OR^a$, —OC(=O)$R^b$, —OC(=O)$NR^bR^c$, —$SO_2R^a$, —$SO_2NR^bR^c$, and/or —$SO_2OR^a$. Examples of groups for $Q^1$, $Q^2$, $Q^3$, and $Q^4$ include H, OH, halo, $N_3$, —$NH_2$, $C_{1-4}$alkyl, —$NR^aSO_2R^a$, and/or $NR^aC$(=O)$OR^a$. Preferably, at least two of $Q^1$, $Q^2$, $Q^3$, and $Q^4$ are H.

In another embodiment, compounds of Formula (I) or pharmaceutically-acceptable salts or stereoisomers thereof, are provided wherein $Q^1$ and $Q^3$ together form —O—, $CR^dR^d$, or a carbon-carbon bond; and $Q^2$ and $Q^4$ are independently H, alkyl, substituted alkyl, hydroxylamine, CN, —C(=O)$R^b$, —C(=O)$NR^bR^c$, and/or —C(=O)$OR^a$.

In one embodiment, compounds of Formula (I) or pharmaceutically-acceptable salts or stereoisomers thereof, are provided wherein $Q^1$ and $Q^3$ together form a carbon-carbon bond, represented by the structure of Formula (Ia):

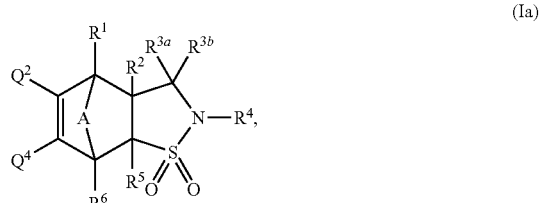

wherein $Q^2$ and $Q^4$ are independently H, alkyl, substituted alkyl, hydroxylamine, CN, —C(=O)$R^b$, —C(=O)$NR^bR^c$, and/or —C(=O)OR$^a$. Compounds of this embodiment include compounds of Formula (Ia) wherein each of Q$^2$ and Q$^4$ are H.

In one embodiment, compounds of Formula (I) or pharmaceutically-acceptable salts or stereoisomers thereof, are provided wherein Q$^1$ and Q$^3$ together form —O—, represented by the structure of Formula (Ib):

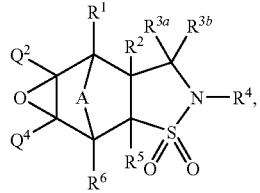

(Ib)

wherein Q$^2$ and Q$^4$ are independently H, alkyl, substituted alkyl, hydroxylamine, CN, —C(=O)R$^b$, —C(=O)NR$^b$R$^c$, and/or —C(=O)OR$^a$. Compounds of this embodiment include compounds of Formula (Ib) wherein each of Q$^2$ and Q$^4$ are H.

In one embodiment, compounds of Formula (I) or pharmaceutically-acceptable salts or stereoisomers thereof, are provided wherein A is —O—, —NR$^8$—, —CR$^{7a}$R$^{7b}$NR$^8$—, or —NR$^8$CR$^{7a}$R$^{7b}$—; and preferably A is —O—, —CR$^{7a}$R$^{7b}$NR$^8$—, or —NR$^8$CR$^{7a}$R$^{7b}$—. This embodiment includes compounds of Formula (I) in which A is CH$_2$NR$^8$— or —NR$^8$CH$_2$. Examples of suitable groups for R$^8$ include H, —C(=O)R$^b$, —C(=O)OR$^a$, and —SO$_2$R$^a$, wherein each of R$^a$ and R$^b$ are independently H, alkyl, substituted alkyl, aryl, substituted aryl, heterocyclo, and/or substituted heterocyclo.

One embodiment provides a compound of Formula (I), wherein said compound is:

rac-4-((1R,2R,6R,7S)-3,3-dioxido-10-oxa-3-thia-4-azatricyclo[5.2.1.0$^{2,6}$]dec-8-en-4-yl)-2-(trifluoromethyl)benzonitrile (1i);

rac-4-((1R,2S,6S,7S)-3,3-dioxido-10-oxa-3-thia-4-azatricyclo[5.2.1.0$^{2,6}$]dec-8-en-4-yl)-2-(trifluoromethyl)benzonitrile (1ii);

4-((1S,2S,6S,7R)-3,3-dioxido-10-oxa-3-thia-4-azatricyclo[5.2.1.0$^{2,6}$]dec-8-en-4-yl)-2-(trifluoromethyl)benzonitrile (2i);

4-((1R,2R,6R,7S)-3,3-dioxido-10-oxa-3-thia-4-azatricyclo[5.2.1.0$^{2,6}$]dec-8-en-4-yl)-2-(trifluoromethyl)benzonitrile (2ii);

4-((1S,2S,6S,7R)-2-methyl-3,3-dioxido-10-oxa-3-thia-4-azatricyclo[5.2.1.0$^{2,6}$]dec-8-en-4-yl)-2-(trifluoromethyl)benzonitrile (3);

4-((1R,2R,6R,7S)-2-methyl-3,3-dioxido-10-oxa-3-thia-4-azatricyclo[5.2.1.0$^{2,6}$]dec-8-en-4-yl)-2-(trifluoromethyl)benzonitrile (4);

4-((1S,2R,6R,7R)-3,3-dioxido-10-oxa-3-thia-4-azatricyclo[5.2.1.0$^{2,6}$]dec-8-en-4-yl)-2-(trifluoromethyl)benzonitrile (5i);

4-((1R,2S,6S,7S)-3,3-dioxido-10-oxa-3-thia-4-azatricyclo[5.2.1.0$^{2,6}$]dec-8-en-4-yl)-2-(trifluoromethyl)benzonitrile (5ii);

4-((1S,2R,6R,7R)-3,3-dioxido-10-oxa-3-thia-4-azatricyclo[5.2.1.0$^{2,6}$]dec-4-yl)-2-(trifluoromethyl)benzonitrile (6);

4-((1R,2S,6S,7S)-3,3-dioxido-10-oxa-3-thia-4-azatricyclo[5.2.1.0$^{2,6}$]dec-4-yl)-2-(trifluoromethyl)benzonitrile (7);

4-((1S,2R,6R,7S,8S,10S)-3,3-dioxido-9,11-dioxa-3-thia-4-azatetracyclo[5.3.1.0$^{2,6}$.0$^{8,10}$]undec-4-yl)-2-(trifluoromethyl)benzonitrile (8);

4-((1R,2S,6S,7R,8R,10R)-3,3-dioxido-9,11-dioxa-3-thia-4-azatetracyclo[5.3.1.0$^{2,6}$.0$^{8,10}$]undec-4-yl)-2-(trifluoromethyl)benzonitrile (9);

rac-4-((1R,2R,6R,7S,9R)-9-hydroxy-3,3-dioxido-10-oxa-3-thia-4-azatricyclo[5.2.1.0$^{2,6}$]dec-4-yl)-2-(trifluoromethyl)benzonitrile (10i);

rac-4-((1R,2R,6R,7R,8S)-8-hydroxy-3,3-dioxido-10-oxa-3-thia-4-azatricyclo[5.2.1.0$^{2,6}$]dec-4-yl)-2-(trifluoromethyl)benzonitrile (10ii);

rac-4-((1R,2R,6R,7R,8R)-8-hydroxy-3,3-dioxido-10-oxa-3-thia-4-azatricyclo[5.2.1.0$^{2,6}$]dec-4-yl)-2-(trifluoromethyl)benzonitrile (10iii);

4-((1S,2R,6R,7R)-3,3-dioxido-10-oxa-3-thia-4-azatricyclo[5.2.1.0$^{2,6}$]dec-4-yl)-2-(trifluoromethyl)benzonitrile (11);

4-((1R,2S,6S,7S)-3,3-dioxido-10-oxa-3-thia-4-azatricyclo[5.2.1.0$^{2,6}$]dec-4-yl)-2-(trifluoromethyl)benzonitrile (12);

4-((1S,2R,6R,7R,9S)-9-hydroxy-3,3-dioxido-10-oxa-3-thia-4-azatricyclo[5.2.1.0$^{2,6}$]dec-4-yl)-2-(trifluoromethyl)benzonitrile (13);

4-((1S,2R,6R,7R,9R)-9-fluoro-3,3-dioxido-10-oxa-3-thia-4-azatricyclo[5.2.1.0$^{2,6}$]dec-4-yl)-2-(trifluoromethyl)benzonitrile (14);

4-((1R,2S,6S,7S,9R)-9-hydroxy-3,3-dioxido-10-oxa-3-thia-4-azatricyclo[5.2.1.0$^{2,6}$]dec-4-yl)-2-(trifluoromethyl)benzonitrile (15);

4-((1R,2S,6S,7S,9S)-9-fluoro-3,3-dioxido-10-oxa-3-thia-4-azatricyclo[5.2.1.0$^{2,6}$]dec-4-yl)-2-(trifluoromethyl)benzonitrile (16);

rac-4-((1R,2R,6R,7S)-1,7-dimethyl-3,3-dioxido-10-oxa-3-thia-4-azatricyclo[5.2.1.0$^{2,6}$]dec-8-en-4-yl)-2-(trifluoromethyl)benzonitrile (17);

rac-4-((1S,2S,6R,7R)-1,7-dimethyl-3,3-dioxido-10-oxa-3-thia-4-azatricyclo[5.2.1.0$^{2,6}$]dec-8-en-4-yl)-2-(trifluoromethyl)benzonitrile (17A);

rac-4-((1R,2R,6R,7S)-1,7-dimethyl-3,3-dioxido-10-oxa-3-thia-4-azatricyclo[5.2.1.0$^{2,6}$]dec-4-yl)-2-(trifluoromethyl)benzonitrile (18);

rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (19);

rac-4-((1S,2R,6S,7R)-7-methyl-3,3-dioxido-5-oxo-10-oxa-3-thia-4-azatricyclo[5.2.1.0$^{2,6}$]dec-8-en-4-yl)-2-(trifluoromethyl)benzonitrile (19A);

rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (20);

rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (21i);

rac-4-((1R,2R,6R,7S)-1-methyl-3,3-dioxido-10-oxa-3-thia-4-azatricyclo[5.2.1.0$^{2,6}$]dec-8-en-4-yl)-2-(trifluoromethyl)benzonitrile (21ii);

rac-4-((1S,2S,6R,7R)-7-methyl-3,3-dioxido-5-oxo-10-oxa-3-thia-4-azatricyclo[5.2.1.0$^{2,6}$]dec-8-en-4-yl)-2-(trifluoromethyl)benzonitrile (21A)

rac-4-((1R,2R,6R,7S)-7-methyl-3,3-dioxido-10-oxa-3-thia-4-azatricyclo[5.2.1.0$^{2,6}$]dec-4-yl)-2-(trifluoromethyl)benzonitrile (22);

rac-4-((1R,2R,6R,7S)-1-methyl-3,3-dioxido-10-oxa-3-thia-4-azatricyclo[5.2.1.0$^{2,6}$]dec-4-yl)-2-(trifluoromethyl)benzonitrile (23);

rac-4-((1R,2R,6R,7R,8S)-8-azido-3,3-dioxido-10-oxa-3-thia-4-azatricyclo[5.2.1.0$^{2,6}$]dec-4-yl)-2-(trifluoromethyl)benzonitrile (24i);

rac-4-((1R,2R,6R,7S,9R)-9-azido-3,3-dioxido-10-oxa-3-thia-4-azatricyclo[5.2.1.0$^{2,6}$]dec-4-yl)-2-(trifluoromethyl)benzonitrile (24ii);

rac-4-((1R,2R,6R,7R,8S)-8-amino-3,3-dioxido-10-oxa-3-thia-4-azatricyclo[5.2.1.0$^{2,6}$]dec-4-yl)-2-(trifluoromethyl)benzonitrile (25i);

rac-4-((1R,2R,6R,7S,9R)-9-amino-3,3-dioxido-10-oxa-3-thia-4-azatricyclo[5.2.1.0$^{2,6}$]dec-4-yl)-2-(trifluoromethyl)benzonitrile (25ii);

methyl rac-(1R,2R,6R,7R,8S)-4-(4-cyano-3-(trifluoromethyl)phenyl)-3,3-dioxido-10-oxa-3-thia-4-azatricyclo[5.2.1.0$^{2,6}$]dec-8-yl)carbamate (26i);

methyl rac-(1R,2R,6R,7S,9R)-4-(4-cyano-3-(trifluoromethyl)phenyl)-3,3-dioxido-10-oxa-3-thia-4-azatricyclo[5.2.1.0$^{2,6}$]dec-9-yl)carbamate (26ii);

benzyl (1S,2S,6S,7R)-4-(4-cyano-3-(trifluoromethyl)phenyl)-10-oxa-3-thia-4-azatricyclo[5.2.1.0$^{2,6}$]decane-2-carboxylate 3,3-dioxide (27);

(1S,2S,6S,7R)-4-(4-cyano-3-(trifluoromethyl)phenyl)-10-oxa-3-thia-4-azatricyclo[5.2.1.0$^{2,6}$]decane-2-carboxylic acid 3,3-dioxide (28);

(1S,2S,6S,7R)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (29);

benzyl (1R,2R,6R,7S)-4-(4-cyano-3-(trifluoromethyl)phenyl)-10-oxa-3-thia-4-azatricyclo[5.2.1.0$^{2,6}$]decane-2-carboxylate 3,3-dioxide (30);

(1R,2R,6R,7S)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (31);

rac-4-((1R,2S,6S,7S)-3,3-dioxido-10-oxa-3-thia-4-azatricyclo[5.2.1.0$^{2,6}$]dec-4-yl)-2-(trifluoromethyl)benzonitrile (32);

rac-(1R,2S,6S,7S)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (33);

rac-4-((1R,2S,6S,7R,8S)-8-hydroxy-3,3-dioxido-10-oxa-3-thia-4-azatricyclo[5.2.1.0$^{2,6}$]dec-4-yl)-2-(trifluoromethyl)benzonitrile (34i);

rac-4-((1R,2S,6S,7S,9R)-9-hydroxy-3,3-dioxido-10-oxa-3-thia-4-azatricyclo[5.2.1.0$^{2,6}$]dec-4-yl)-2-(trifluoromethyl)benzonitrile (34ii);

rac-4-((1R,2S,6S,7R,8R)-8-hydroxy-3,3-dioxido-10-oxa-3-thia-4-azatricyclo[5.2.1.0$^{2,6}$]dec-4-yl)-2-(trifluoromethyl)benzonitrile (34-iii);

rac-4-((1R,2S,6S,7S,9S)-9-hydroxy-3,3-dioxido-10-oxa-3-thia-4-azatricyclo[5.2.1.0$^{2,6}$]dec-4-yl)-2-(trifluoromethyl)benzonitrile (34iv);

rac-4-((1R,2S,6S,7R,8R)-8-fluoro-3,3-dioxido-10-oxa-3-thia-4-azatricyclo[5.2.1.0$^{2,6}$]dec-4-yl)-2-(trifluoromethyl)benzonitrile (35i);

rac-4-((1R,2S,6S,7S,9S)-9-fluoro-3,3-dioxido-10-oxa-3-thia-4-azatricyclo[5.2.1.0$^{2,6}$]dec-4-yl)-2-(trifluoromethyl)benzonitrile (35ii);

4-((1S,2R,6R,7S,8S)-8-fluoro-3,3-dioxido-10-oxa-3-thia-4-azatricyclo[5.2.1.0$^{2,6}$]dec-4-yl)-2-(trifluoromethyl)benzonitrile (36i);

4-((1R,2S,6S,7R,8R)-8-fluoro-3,3-dioxido-10-oxa-3-thia-4-azatricyclo[5.2.1.0$^{2,6}$]dec-4-yl)-2-(trifluoromethyl)benzonitrile (36ii);

4-((1S,2R,6R,7S,8S)-8-hydroxy-3,3-dioxido-10-oxa-3-thia-4-azatricyclo[5.2.1.0$^{2,6}$]dec-4-yl)-2-(trifluoromethyl)benzonitrile (37i);

4-((1R,2S,6S,7R,8R)-8-hydroxy-3,3-dioxido-10-oxa-3-thia-4-azatricyclo[5.2.1.0$^{2,6}$]dec-4-yl)-2-(trifluoromethyl)benzonitrile (37ii);

4-((1S,2R,6R,7R,9R)-9-hydroxy-3,3-dioxido-10-oxa-3-thia-4-azatricyclo[5.2.1.0$^{2,6}$]dec-4-yl)-2-(trifluoromethyl)benzonitrile (38i);

4-((1R,2S,6S,7S,9S)-9-hydroxy-3,3-dioxido-10-oxa-3-thia-4-azatricyclo[5.2.1.0$^{2,6}$]dec-4-yl)-2-(trifluoromethyl)benzonitrile (38ii);

rac-4-((1R,2S,6S,7R,8R)-8-azido-3,3-dioxido-10-oxa-3-thia-4-azatricyclo[5.2.1.0$^{2,6}$]dec-4-yl)-2-(trifluoromethyl)benzonitrile (39i);

rac-4-((1R,2S,6S,7S,9S)-9-azido-3,3-dioxido-10-oxa-3-thia-4-azatricyclo[5.2.1.0$^{2,6}$]dec-4-yl)-2-(trifluoromethyl)benzonitrile (39ii);

methyl ((1S,2R,6R,7S,8S)-4-(4-cyano-3-(trifluoromethyl)phenyl)-3,3-dioxido-10-oxa-3-thia-4-azatricyclo[5.2.1.0$^{2,6}$]dec-8-yl)carbamate (40i);

methyl((1R,2S,6S,7R,8R)-4-(4-cyano-3-(trifluoromethyl)phenyl)-3,3-dioxido-10-oxa-3-thia-4-azatricyclo[5.2.1.0$^{2,6}$]dec-8-yl)carbamate (40ii);

methyl((1S,2R,6R,7R,9R)-4-(4-cyano-3-(trifluoromethyl)phenyl)-3,3-dioxido-10-oxa-3-thia-4-azatricyclo[5.2.1.0$^{2,6}$]dec-9-yl)carbamate (4ii);

methyl((1R,2S,6S,7S,9S)-4-(4-cyano-3-(trifluoromethyl)phenyl)-3,3-dioxido-10-oxa-3-thia-4-azatricyclo[5.2.1.0$^{2,6}$]dec-9-yl)carbamate (41ii);

rac-benzyl (1S,2S,6R,7S)-4-(4-cyano-3-(trifluoromethyl)phenyl)-3-thia-4,8-diazatricyclo[5.2.2.0$^{2,6}$]undec-10-ene-8-carboxylate 3,3-dioxide (42);

rac-benzyl (1S,2S,6S,7S)-4-(4-cyano-3-(trifluoromethyl)phenyl)-5-oxo-3-thia-4,8-diazatricyclo[5.2.2.0$^{2,6}$]undec-10-ene-8-carboxylate 3,3-dioxide (42B);

rac-benzyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide (43);

rac-4-((1R,2R,6S,7R)-3,3-dioxido-3-thia-4,8-diazatricyclo[5.2.2.0$^{2,6}$]undec-4-yl)-2-(trifluoromethyl)benzonitrile (44);

rac-4-((1R,2R,6S,7R)-8-acetyl-3,3-dioxido-3-thia-4,8-diazatricyclo[5.2.2.0$^{2,6}$]undec-4-yl)-2-(trifluoromethyl)benzonitrile (45);

rac-4-((1R,2R,6S,7R)-8-(ethylsulfonyl)-3,3-dioxido-3-thia-4,8-diazatricyclo[5.2.2.0$^{2,6}$]undec-4-yl)-2-(trifluoromethyl)benzonitrile (46);

methyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide (47); or phenyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide (48);

or a pharmaceutically-acceptable salt or stereoisomer thereof.

Methods of Preparation

In general, the compounds of Formula (I) can be prepared in accordance with the following Schemes and the general knowledge of one skilled in the art and/or using methods set forth in the Examples that follow. Solvents, temperatures, pressures, and other reaction conditions can readily be selected by one of ordinary skill in the art. Starting materials are commercially available or readily prepared by one skilled in the art. Combinatorial techniques can be employed in the preparation of compounds, for example, where the intermediates possess groups suitable for these techniques. In the schemes, the groups A, $Q^1$, $Q^2$, $Q^3$, $Q^4$, $R^1$, $R^2$, $R^{3a}$, $R^{3b}$, $R^4$, $R^5$, and $R^6$ are described hereinabove.

Scheme 1

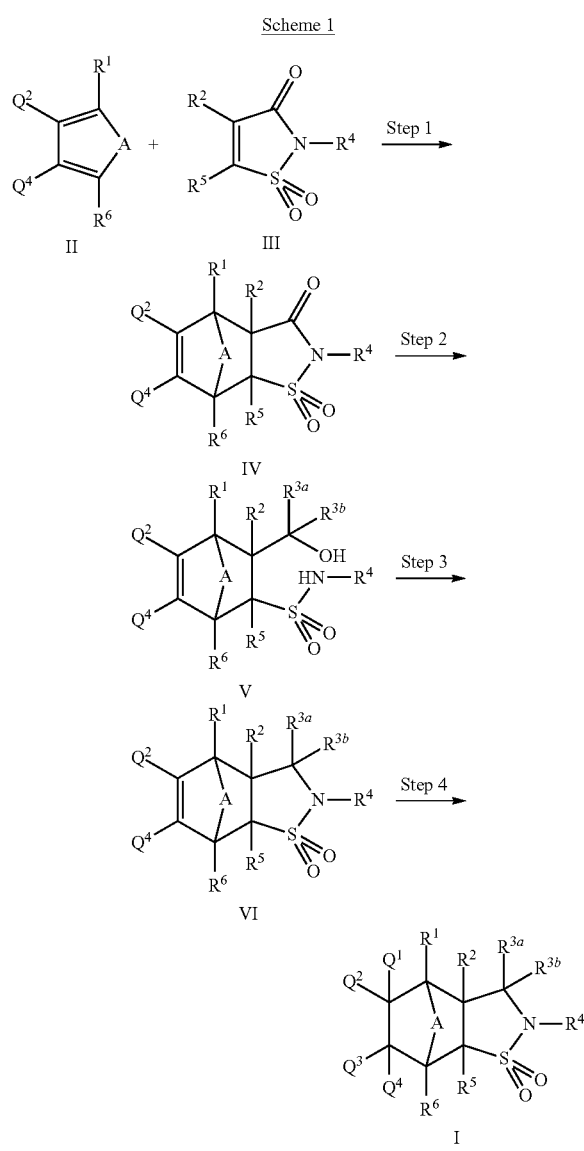

Step 1

A diene of the general Formula II and a dienophile of the general Formula III can undergo a [4+2] cycloaddition under thermal or Lewis acidic conditions in a solvent, such as, for example, THF and/or toluene to generate compounds of the general Formula IV.

A diene of general Formula II can be obtained either from commercial sources, or can be readily made by one of skill in the art, for example, in accordance with the following publication and references found therein: Derrick L. J. Clive et al., *Tetrahedron*, 60:4205-4221 (2004). Representative methods of preparation of dienophiles of general Formula III are discussed below in Schemes 3 and 4.

Step 2

Compounds of general Formula IV can be treated under reductive conditions, such as, for example, sodium borohydride in a solvent system of THF/MeOH to yield an alcohol of general Formula V.

Step 3

Compounds of general Formula V can undergo cyclization under a variety of conditions including, but not limited to, for example, an intramolecular Mitsunobu reaction by treating the Formula V compound with, for example, triphenylphosphine and diisopropylazodicarboxylate in THF to yield a compound of general Formula VI. A Formula V compound may also be treated with an activating agent, such as, for example, para-toluenesulfonyl chloride, followed by a strong base, such as, for example, lithium diisopropylamide to afford a cyclized compound in accordance with Formula VI.

When $R^{3a}$ or $R^{3b}$ is hydrogen, a compound of Formula VI can be treated with a strong base, such as, for example, lithium diisopropylamide to generate an anion that can react with various electrophiles, such as, for example, methyl iodide and methyl chloroformate, to produce a compound of the general Formula VI where $R^{3a}$ or $R^{3b}$ is the corresponding alkyl or acyl group.

Step 4

A compound of the general Formula I can be produced by functionalizing the olefin of the Formula VI compound via a variety of methods known to one skilled in the art. Such functionalization methods include, but are not limited to, for example, dihydroxylation; aminohydroxylation; hydrogenation; hydroxylation; hydroboration and subsequent oxidation; epoxidation; aziridination; cyclopropanation; bromination; and chlorination. The resulting products may undergo further functional group manipulations, including, but not limited to, for example, converting a hydroxyl group to a fluoro functionality by treating with DAST; and reducing an azide to the corresponding amine and further derivatizing to alkyl carbamates, amides, sulfonamides or ureas. Other well-known methods for functionalizing an olefin can be found in standard synthetic organic references, such as, for example, Larock, R. C., *Comprehensive Organic Transformations*, VCH Publishers, New York (1989) and March, J., *Advanced Organic Chemistry*, John Wiley & Sons Inc. USA (1985).

Compounds of Formula VI or I in which the group $R^{3a}$ (or $R^{3b}$) is an ester, can be hydrolyzed to the corresponding carboxylic acid by being reacted with a reagent, such as, for example, lithium hydroxide in a solvent, such as, for example, THF. The acid may subsequently be converted to a variety of alkyl amides under standard conditions, e.g., treating with oxalyl chloride followed by reaction with the corresponding amine. The carboxylic acid may also be reduced to the corresponding alcohol or subjected to Curtius rearrangement conditions to provide a primary amine for further functional group manipulations.

Scheme 2

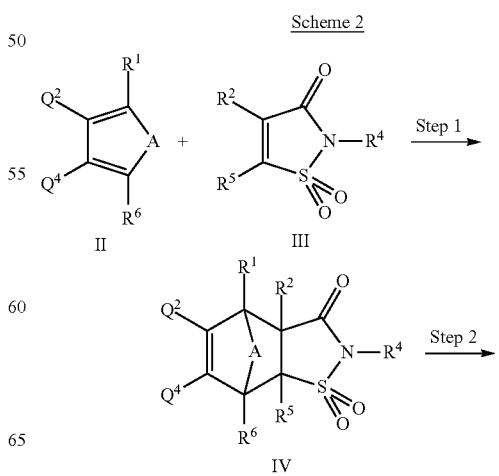

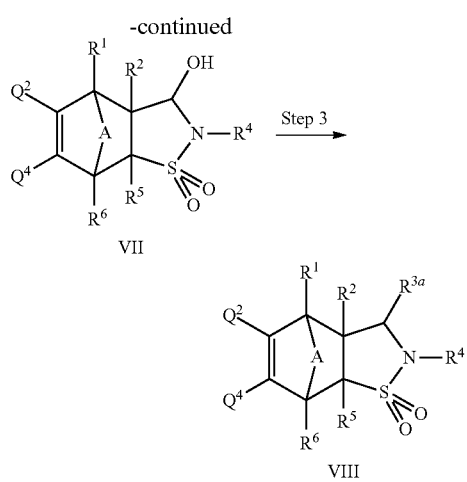

Step 1

Compounds of general Formula IV can be prepared in accordance with the procedure outlined in Step 1 of Scheme 1.

Step 2

Compounds of general Formula VII can be produced by treating a compound of general Formula IV with an appropriate reducing agent, such as, for example, diisobutylaluminum hydride in a solvent, such as, for example, toluene.

Step 3

Compounds of general Formula VII can be treated with an appropriate reagent, such as, for example, trimethylaluminum and allyltrimethylsilane followed by reaction with a reagent, such as, for example, boron trifluoride etherate to produce the corresponding alkylated compound of Formula VIII. The olefin of a Formula VIII compound can be further functionalized in accordance with the procedures described in step 4 of Scheme 1.

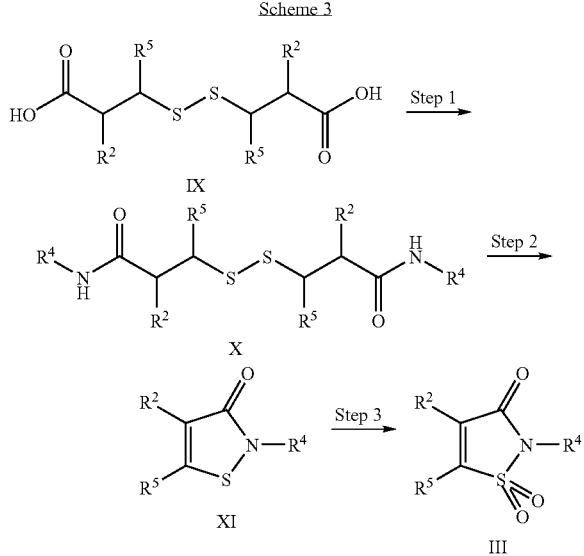

Step 1

Appropriately substituted dithiopropionic acid IX may be commercially available; or in the alternative can be prepared in accordance with synthetic routes described in the literature, e.g., Lewis S. N. et al., *J. Heterocyclic Chem.* 8:571-580 (1971). The diacid IX can be converted to the corresponding bis-amide X via a 2-step sequence involving a) first reacting the diacid IX with a reagent, such as, for example, thionyl chloride in the presence of a suitable catalyst, such as, for example, pyridine to produce the corresponding bis-acid chloride, and b) subsequently treating the bis-acid chloride with an appropriate amine in a solvent, such as, for example, THF to provide bis-amide X.

Step 2

Bis-amide X can be cyclized to a compound of Formula XI by reacting bis-amide X with a reagent, such as, for example, sulfuryl chloride in a solvent, such as, for example, toluene.

Step 3

A dienophile in accordance with Formula III can be produced by the oxidization of a compound of Formula XI. Such oxidation can be effectuated by, for example, reacting a Formula XI compound with a reagent, such as, for example, meta-chloroperoxybenzoic acid in a solvent, such as, for example, dichloromethane.

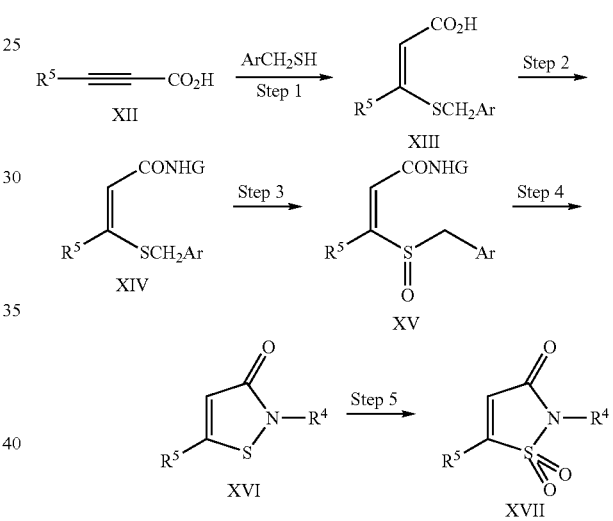

Scheme 4 illustrates a method for synthesizing a Formula XVII dienophile, which is a Formula III dienophile in which one $R^3$ is a H, e.g., see Beeley, N. R. A. et al., *J. Chem. Soc. Perkin Trans. I*, 2245-2251 (1994).

Step 1

A propenoic acid in accordance with Formula XIII can be produced by heating a propynoic acid in accordance with Formula XII with a benzylthiol in the presence of a base, such as, for example, sodium carbonate and a solvent, such as, for example, ethanol.

Step 2

The Formula XIII propenoic acid can be converted to the corresponding amide of Formula XIV via successive reactions with an acid chloride, such as, for example, oxalyl chloride and an appropriate amine Step 3

The corresponding sulfoxide of Formula XV can be produced by reacting the Formula XIV compound with an oxidizing agent, such as, for example, 1 equivalent of m-CPBA.

Step 4

The Formula XV compound can be cyclized to the isothiazolone of Formula XVI by reacting the Formula XV compound with a reagent, such as, for example, trichloroacetic anhydride in a solvent, such as, for example, dichloromethane.

Step 5

The isothiazolone of Formula XVI can be oxidized to the dienophile XVII in accordance with the procedure described in step 3 of Scheme 3.

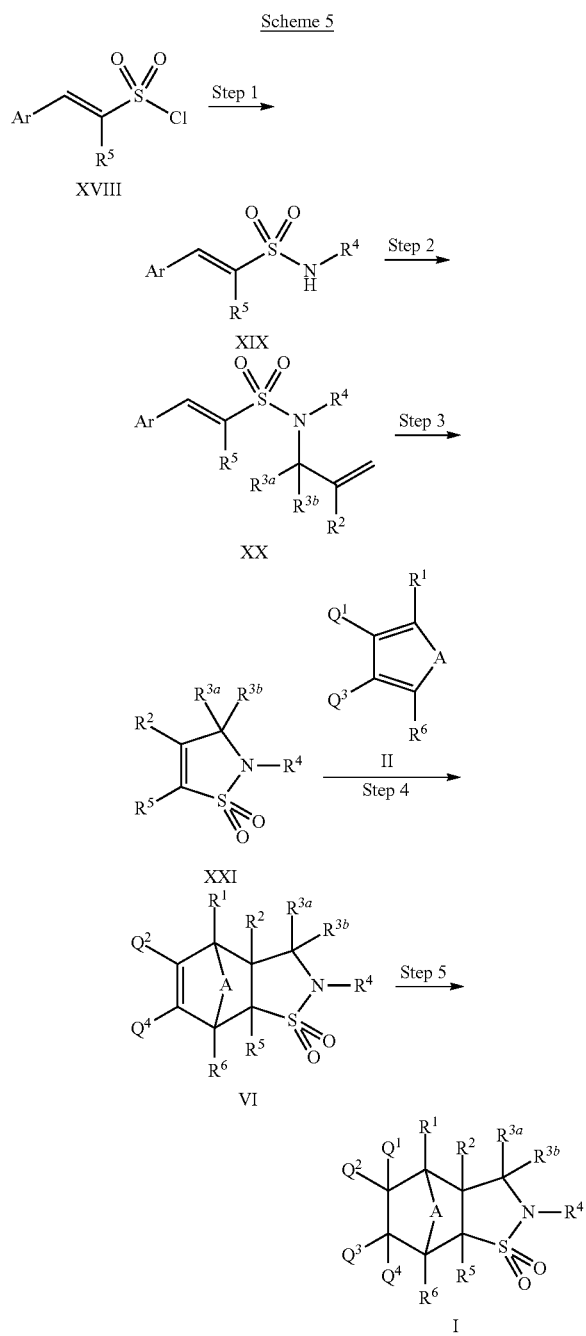

Scheme 5

Alternatively, compounds in accordance with Formula I can be synthesized in accordance with Scheme 5. The dienophile of Formula XXI can be prepared in accordance with a procedure reported in the literature (Harned, A. M. et al., *Org. Leu.*, 5:15-18 (2003)).

Step 1

A sulfonamide in accordance with Formula XIX can be produced by treating a styrene sulfonyl chloride in accordance with Formula XVIII with an appropriate amine in a solvent, such as, for example, pyridine.

Step 2

A compound in accordance with Formula XX can be obtained by alkylating the Formula XIX sulfonamide with a suitable electrophile, such as, for example, allyl bromide in the presence of reagents, such as, for example, potassium carbonate and potassium iodide in a solvent, such as, for example, acetonitrile.

Step 3

The Formula XX compound can be subjected to olefin metathesis by being heated in the presence of an appropriate catalyst, such as, for example, $(PCy_3)_2Cl_2Ru=CHPh$ to provide a cyclized compound in accordance with Formula XXI.

Step 4

The dienophile of Formula XXI can undergo a [4+2] cycloaddition with an appropriately substituted diene II in the presence of a catalyst, such as, for example, diethylaluminum chloride in a solvent, such as, for example, toluene to afford a compound in accordance with Formula V.

Step 5

The Formula V compound can be converted to a compound in accordance with Formula VI as described in step 4 of Scheme 1.

The nuclear hormone receptor (NHR) family includes the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHRs, the Orphan receptors, as well as other NHRs.

The terms "modulate", "modulates", "modulating", or "modulation", as used herein, refer to, for example, the activation (e.g., agonist activity) or inhibition (e.g., antagonist activity) of at least one NHR.

The term "NHR-associated condition(s)", as used herein, denotes a condition or disorder that can be treated by modulating the function of at least one NHR associated with the condition or disorder. The treatment comprises preventing, partially alleviating, or curing the condition or disorder. Modulation may occur either locally, for example, within certain tissues of the subject being treated, or more extensively throughout the subject.

The compounds of Formula (I) are useful for modulating the function of a nuclear hormone receptor specifically, the androgen receptor (AR). Formula (I) compounds are useful to treat AR-associated conditions. In one embodiment, at least one compound of Formula (I) selectively modulates the androgen receptor within the NHR family.

Compounds of Formula (I) may be used to treat a variety of medical conditions and/or disorders associated with the AR pathway. Formula (I) compounds can modulate the function of the AR by, for example, agonizing, partially agonizing, antagonizing, and/or partially antagonizing the AR. In one embodiment, at least one compound of Formula (I) selectively modulates the function of at least one AR. In another embodiment, at least one compound of Formula (I) agonizes or partially agonizes the function of at least one AR. In still another embodiment, at least one compound of Formula (I) antagonizes or partially antagonizes the function of at least one AR.

Medical conditions associated with the AR pathway include, but are not limited to, for example, benign prostate hyperplasia, hirsutism, acne, hyperpilosity, seborrhea, endometriosis, polycystic ovary syndrome, androgenic alopecia, adenomas and neoplasies of the prostate, benign or malignant tumor cells containing the androgen receptor, hypogonadism, osteoporosis, suppression of spermatogenesis, libido, cachexia, anorexia, androgen supplementation for age related decreased testosterone levels in men, prostate cancer, breast cancer, endometrial cancer, uterine cancer, hot flashes, and Kennedy's disease. For example, pan AR modulation is contemplated, with prostate selective AR modulation ("SARM") being particularly preferred, such as for the treatment of early stage prostate cancers. In one embodiment, Compound (I) is used to treat prostate cancer by being employed as an antagonist or partial antagonist of the AR.

Formula (I) compounds can be used to antagonize, preferably selectively antagonize, mutated ARs found, for example, in many tumor cell lines. Exemplary mutated ARs, include, but are not limited to, those found in prostate tumor cell lines, such as, for example, LNCap (T877A mutation, *Biophys. Acta*, 187:1052 (1990)); PCa2b (L701H & T877A mutations, *J. Urol.*, 162:2192 (1999)); and CWR22 (H874Y mutation, *Mol. Endo.*, 11:450 (1997)).

One embodiment provides a pharmaceutical composition comprising at least one compound in accordance with Formula (I), or a pharmaceutically-acceptable salt or stereoisomer thereof; optionally at least one pharmaceutically-acceptable carrier and/or diluent; and optionally at least one other anti-cancer agent.

A still further embodiment provides a method for treating at least one condition or disorder comprising administering to a patient in need thereof a therapeutically effective amount of at least one compound of Formula (I), or a pharmaceutically-acceptable salt or stereoisomer thereof; optionally administering either simultaneously or sequentially at least one other anti-cancer agent, and optionally administering either simultaneously or sequentially at least one other anti-cancer treatment.

The phrase "other anti-cancer agent" includes any known agent useful for treating cancer, preferably prostate cancer.

In treating cancer, a combination of chemotherapeutic agents and/or other treatments (e.g., radiation therapy) is often advantageous. The other anti-cancer agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, the compounds of formula (I) (or other formulae disclosed herein) may be administered in combination with other anti-cancer agents and treatments useful in the treatment of cancer or other proliferative diseases. The invention herein further comprises use of the compounds of formula I herein (or other formulae disclosed herein), in preparing medicaments for the treatment of cancer, and/or it comprises the packaging of the compounds of formula (I) herein together with instructions that the compounds be used in combination with other anti-cancer agents and treatments for the treatment of cancer. The present invention further comprises combinations of the compounds of formula (I) and one or more additional agents in kit form, e.g., where they are packaged together or placed in separate packages to be sold together as a kit, or where they are packaged to be formulated together.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of Formula (I) can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The phrase "anti-cancer treatment" includes but is not limited to, for example, radiation therapy and surgery, e.g., castration.

In one embodiment, at least one compound of Formula (I) is used to treat cancer.

The cancers that can be treated using Formula (I) compound(s) include, but are not limited to, for example, carcinoma, including, for example, that of the bladder, breast, colon, kidney, liver, lung (including small cell lung cancer), esophagus, gall bladder, ovary, pancreas, stomach, cervix, thyroid, prostate, and skin (including squamous cell carcinoma); hematopoietic tumors of lymphoid lineage, such as, for example, leukemia, acute lymphocytic leukemia, acute lymphoblastic leukemia, B-cell lymphoma, T-cell lymphoma, Hodgkin lymphoma, non-Hodgkin lymphoma, hairy cell lymphoma, and Burkett's lymphoma; hematopoietic tumors of myeloid lineage, such as, for example, acute and chronic myelogenous leukemia, myelodysplastic syndrome, and promyelocytic leukemia; tumors of mesenchymal origin, including, for example, fibrosarcoma and rhabdomyosarcoma; tumors of the central and peripheral nervous system, including, for example, astrocytoma, neuroblastoma, glioma, and schwannomas; and other tumors, such as, for example, melanoma, seminoma, teratocarcinoma, osteosarcoma, xeroderma pigmentosum, keratoacanthoma, thyroid follicular cancer, and Kaposi's sarcoma.

In another embodiment, at least one compound of Formula (I) is used to treat prostate cancer, breast cancer, uterine cancer, and/or endometrial cancer.

In another embodiment, at least one compound of Formula (I) is used to treat prostate cancer.

In yet another embodiment, at least one compound of Formula (I) is used to treat adenoma(s) and neoplasie(s) of the prostate.

In one embodiment, the patient is a mammal, including, but not limited to, for example, humans and domestic animals, such as, for example, dogs, cats, and horses.

In yet a further embodiment, the patient is a human.

Compounds in accordance with Formula (I) may be used, for example, in combination with known therapies for treating advanced metastatic prostate cancer including, but not limited to, for example, "complete androgen ablation therapy" wherein tumor growth is inhibited by controlling the supply of androgen to the prostate tissues via chemical castration followed by the administration of at least one AR antagonist. The compounds of Formula (I) can be employed as AR antagonists in complete ablation therapy, alone or in combination with other AR antagonists such as Flutamide, bicalutamide, Nilutamide, or Cyproterone acetate.

The compounds of Formula (I) may further be employed adjuvant to surgery.

Compounds in accordance with Formula (I) may be used, for example, either in combination with antibody therapy including, but not limited to, for example, antibody therapy against PSCA, or in concert with vaccine/immune modulating agents used to treat cancer.

Compounds in accordance with Formula (I) can be administered by any means suitable for the condition to be treated, which can depend on the need for site-specific treatment or quantity of Formula (I) compound to be delivered.

Any pharmaceutical composition contemplated herein can, for example, be delivered orally via any acceptable and suitable oral preparations. Exemplary oral preparations, include, but are not limited to, for example, tablets; troches; lozenges; aqueous or oily suspensions; dispersible powders or granules; emulsions; hard or soft capsules; syrups; and elixirs. Pharmaceutical compositions intended for oral administration can be prepared according to any methods known in the art for manufacturing pharmaceutical compositions intended for oral administration. In order to provide pharmaceutically elegant and palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinylpyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate buryrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and a hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oil phase can be provided by, but is not limited to, for example, a vegetable oil, such as, for example, olive oil and arachis oil; a mineral oil, such as, for example, liquid paraffin; and mixtures thereof. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. An emulsion can also contain a sweetening agent, a flavoring agent, a preservative, and/or an antioxidant.

Any pharmaceutical composition contemplated herein can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleagenous suspensions.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile nontoxic acceptable solvent or suspending medium, such as, for example, sterile fixed oils, e.g., synthetic mono- or diglycerides; and fatty acids, such as, for example, oleic acid.

Any pharmaceutical composition contemplated herein can, for example, further be administered via any acceptable and suitable rectal preparation, including, but not limited to, for example, a suppository. A suppository can be prepared by mixing at least one compound of Formula (I) with at least one suitable non-irritating excipient that is liquid at rectal temperatures but solid at a temperature below rectal temperature. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Any pharmaceutical composition contemplated herein can, for example, be administered via any acceptable and suitable topical preparations including, but not limited to, for example, creams; ointments; jellies; solutions; suspensions, transdermal patches; and intranasal inhalers. For purposes of this application, topical preparations include mouth washes and gargles.

Exemplary compositions for nasal aerosol or inhalation administration include solutions that may contain, for example, benzyl alcohol or other suitable preservatives, absorption promoters to enhance absorption and/or bioavailability, and/or other solubilizing or dispersing agents such as those known in the art.

An "effective amount" of Formula (I) compound may be determined by one of ordinary skill in the art, and includes exemplary dosage amounts for a mammal of from about 1 to about 500 mg/day, preferably from about 5 to about 300 mg/day, and more preferably, from about 10 to about 200 mg/day, in a single dose or in or in the form of individual divided doses. Exemplary dosage amounts for an adult human are from about 20, 40, 60, 80, 100, and 120 mg active compound per day, which can be administered in a single dose or in the form of individual divided doses, such as from 1 to 4 times per day.

The specific dose level and frequency of dosage for any particular subject, however, may be varied and generally depends on a variety of factors, including, but not limited to, for example, the bioavailability of the specific Formula (I) compound(s) in the administered form; metabolic stability and length of action of the specific Formula (I) compound(s); species, age, body weight, general health, sex, and diet of the subject; mode and time of administration; rate of excretion; drug combination; and severity of the particular condition.

The compounds of Formula (I) can also be formulated or co-administered with other therapeutic agents that are selected for their particular usefulness in administering therapies associated with the aforementioned conditions. For example, the compounds of the invention may be formulated with agents to prevent nausea, hypersensitivity, and/or gastric irritation, such as, for example, antiemetics and $H_1$ and $H_2$ antihistaminics.

The above other therapeutic agents, when employed in combination with the compounds of Formula (I), can be used, for example, in those amounts indicated in the Physicians' Desk Reference (PDR) or as otherwise determined by one of ordinary skill in the art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

ABBREVIATIONS

| | |
|---|---|
| DCM = | dichloromethane |
| DIAD = | diisopropyl azodicarboxylate |
| DMA = | dimethylamine |
| EtOH = | ethanol. |
| EtOAc = | ethyl acetate |
| HPLC = | high pressure chromatography |
| LiHMDS = | lithium bis(trimethylsilyl)amide |
| mCPBA = | 3-chloroperoxybenzoic acid (approx. 77%) |
| MeOH = | methanol |
| PhMe = | |
| Pd/C = | palladium on carbon |
| RT = | room temperature |
| THF = | tetrahydrofuran |

Examples 1i and 1ii rac-4-((1R,2R,6R,7S)-3,3-dioxido-10-oxa-3-thia-4-azatricyclo[5.2.1.0²,⁶]dec-8-en-4-yl)-2-(trifluoromethyl)benzonitrile (1i) and rac-4-((1R,2S,6S,7S)-3,3-dioxido-10-oxa-3-thia-4-azatricyclo[5.2.1.0²,⁶]dec-8-en-4-yl)-2-(trifluoromethyl)benzonitrile (1ii)

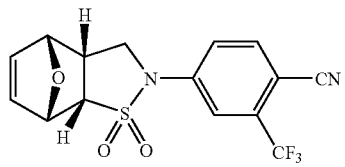
(1i)

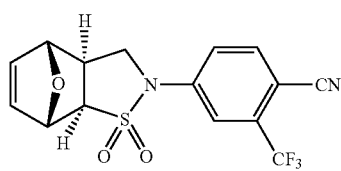
(1ii)

Step A: 3,3'-disulfanediyldipropanoyl chloride (1A)

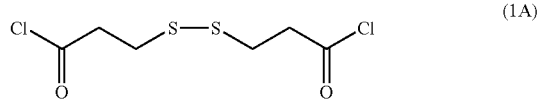 [SMILES: O=C(Cl)CCSSCCC(=O)Cl]
(1A)

Thionyl chloride (69.2 mL, 951 mmol) was added to a mixture of dithiopropionic acid (50.0 g, 238 mmol) and pyridine (0.1 mL) at 22° C. followed by stirring for 16 hours. The reaction mixture was vented into a scrubbing solution of KOH in water to trap the resulting HCl produced in this reaction. The mixture started out heterogeneous and became a clear amber solution after stirring overnight. The mixture was concentrated in vacuo to give 62 g of Compound 1A as a yellow oil. This was stored under argon at 0° C.

Step B: 3,3'-disulfanediylbis(N-(4-cyano-3-(trifluoromethyl)phenyl) propanamide) (1B)

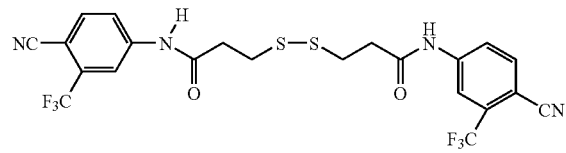
(1B)

To a clear amber solution of 2-trifluoromethyl 4-aminobenzonitrile (14.9 g; 80.8 mmol; 2.0 equiv) in 80 mL dry THF at 22° C. was added Compound 1A (10.0 g; 40.4 mmol; 1.0 equiv), neat, by syringe. A slight exotherm was observed. The homogeneous amber solution stirred for 20 minutes, then placed in a 55° C. oil bath for 30 minutes. HPLC indicated only a small amount of aniline was present. The contents of the reactor were concentrated in vacuo, yielding a tan solid. After absorption onto silica, the crude material was purified by flash column chromatography (1% acetone/DCM to elute aniline, then 10-50% acetone/DCM to elute desired as a pale yellow band.) 20.3 g (94%) of Compound 1B was obtained as an off-white solid.

95% at 3.736 min (retention times) (YMC ODS-A column 4 6×50 mm eluting with 10-90% aqueous methanol over 4 minutes containing 0.1% $H_3PO_4$, 4 mL/min, monitoring at 220 nm).

Step C: 4-(3-oxo-2(3H)-isothiazolyl)-2-(trifluoromethyl)benzonitrile (1C)

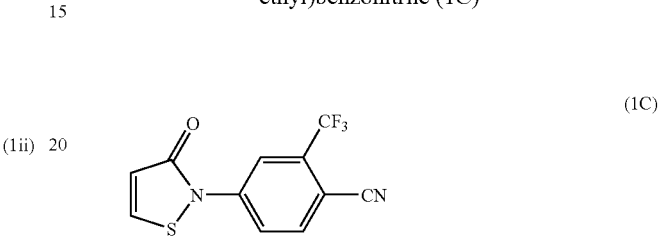
(1C)

To a suspension of Compound 1B (13.0 g, 23.8 mmol) in toluene (50 mL) at 50° C. was added sulfuryl chloride (5.80 mL, 71.3 mmol) in toluene (10 mL) via addition funnel over 0.5 hour. The reaction mixture became clear and then cloudy and viscous after the addition was complete. After six additional hours, the reaction mixture was cooled to 22° C. and filtered rinsing with toluene. The resulting white solid was briefly dried under high vacuum followed by slurrying with water. The resulting slurry was stirred for 10 minutes followed by filtration and drying under high vacuum. After drying, 10.9 g (85%) of Compound 1C was isolated as a pale yellow solid. HPLC purity was >95%.

98% at 2.575 min (retention times) (YMC ODS-A column 4 6×50 mm eluting with 10-90% aqueous methanol over 4 minutes containing 0.1% $H_3PO_4$, 4 mL/min, monitoring at 220 nm). MS (ES): m/z 269.06 [M−H]⁻.

Step D: 4-(1,1-dioxido-3-oxo-2(3H)-isothiazolyl)-2-(trifluoromethyl)benzonitrile

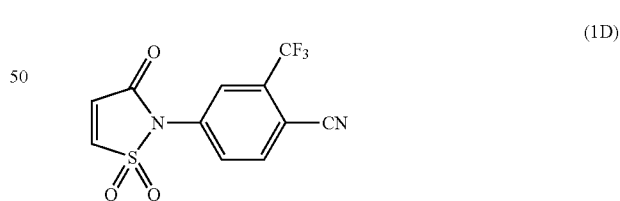
(1D)

Compound 1C (10.00 g, 37.0 mmol) was dissolved in $CH_2Cl_2$ (400 mL) and mCPBA (77%, 20.0 g, 81.5 mmol) was added at 22° C. After 10 minutes, LC-MS showed no starting material remained. After 20 minutes, 3-hydroxypyridine (3.51 g, 37.0 mmol) was added over a 2 minute period with vigorous stirring producing a slight exotherm. After 5 minutes, saturated aqueous $NaHCO_3$ (300 mL) was added with vigorous stirring. After stirring for 5 minutes, the solution was transferred to a separatory funnel and the organic layer was then separated. The organic phase was then washed once with a 1:1 solution of brine and saturated aqueous $NaHCO_3$ (300 mL) and then dried over anhydrous Na$_2$SO$_4$. Concentration in vacuo gave 10.2 g of Compound 1D as a pale yellow solid.

99% at 2.680 min (retention times) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 301.02 [M−H]$^-$.

Step E

A reaction mixture was prepared by adding Compound 1D (1.0 g, 3.3 mmol) to furan (10 mL) at 22° C. The reaction mixture was stirred at 22° C. for 1 hour. The reaction mixture was then concentrated to give 0.50 g of mixture of endo and exo cycloaddition products. The mixture was then dissolved in tetrahydrofuran (THF, 5 mL) and methanol (5 mL) at 22° C. NaBH$_4$ (0.25 g, 6.6 mmol) was added. The resulting reaction mixture was stirred for 30 minutes, acidified by addition of saturated NH$_4$Cl solution (50 mL), and then extracted with CH$_2$Cl$_2$ (3×50 mL). The organic phases were combined, dried over anhydrous sodium sulfate and filtered. The filtrate was concentrated in vacuo to give the crude ring opened alcohol-sulfonamide intermediate as a white solid (0.37 g). This alcohol was then dissolved in THF (5 mL). Triphenyl phosphine (0.53 g, 2.0 mmol) was added followed by diisopropyl azodicarboxylate (0.40 mL, 2.0 mmol). The reaction mixture was stirred at 22° C. under nitrogen for 10 minutes, and then concentrated in vacuo to give a crude mixture of racemic Example 1i and racemic Example 1ii, which were purified by flash chromatography using an ISCO system with a 120 g column, Flow rate: 85 mL/min, solvent A: dichloromethane, solvent B: EtOAc. Gradient: 0% B to 20% B in 25 minutes to give 0.16 g of Example 1i as a white solid and 0.080 g of Example 1ii as a white solid.

Example 1i: 99% at 2.72 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 415.16 [M+H-OAc]$^-$.

Example 1ii: 99% at 2.57 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 415.16 [M+H-OAc]$^-$.

Examples 2i and 2ii 4-((1S,2S,6S,7R)-3,3-dioxido-10-oxa-3-thia-4-azatricyclo[5.2.1.0$^{2,6}$]dec-8-en-4-yl)-2-(trifluoromethyl)benzonitrile (2i) and 4-((1R,2R,6R,7S)-3,3-dioxido-10-oxa-3-thia-4-azatricyclo[5.2.1.0$^{2,6}$]dec-8-en-4-yl)-2-(trifluoromethyl)benzonitrile (2ii)

(2i)
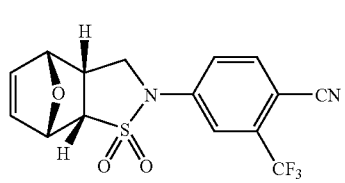

(2ii)
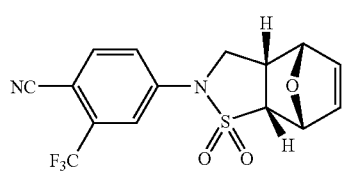

The racemic mixture of Example 1i was separated into individual antipodes by use of a Chiralpack AD column (250× 4.6 mm, 10 um), flow rate: 2.0 mL/min, Detector wavelength: 220 nm. Mobile Phase:CO2/MeOH-ACN (50/50). Example 2i was eluted at 4.4 minutes and Example 2ii was eluted at 5.3 minutes. Absolute stereochemistry is unknown.

Example 3

4-((1S,2S,6S,7R)-2-methyl-3,3-dioxido-10-oxa-3-thia-4-azatricyclo[5.2.1.0$^{2,6}$]dec-8-en-4-yl)-2-(trifluoromethyl)benzonitrile

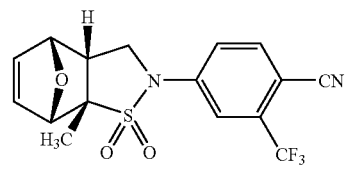 [SMILES: C[C@@]12[C@@H]3C=C[C@@H](O3)[C@@H]1CN(c1ccc(C#N)c(C(F)(F)F)c1)S2(=O)=O]

A solution of Example 2i (30 mg; 0.08 mmol) in 1 mL dry THF was then added lithium diisopropylamide (0.094 mL, 1.8M in THF, 0.17 mmol). The resulting clear orange solution was stirred 10 minutes. Iodomethane (15 μL; 0.24 mmol) was then added, and the solution slowly warmed to ambient temperature. The reaction was quenched with saturated aqueous NH$_4$Cl and EtOAc and water added. The layers were separated and the aqueous phase extracted twice with 4 mL EtOAc. The organics were combined, washed with brine, dried (MgSO$_4$), filtered, and concentrated in vacuo revealing crude material in 89% purity by HPLC. The crude material was dissolved in MeOH and purified by preparative HPLC and flash chromatography using an ISCO system (Isco, Inc., Lincoln, Nebr.) with a 4 g column, Flow rate: 30 mL/min, solvent A: CH$_2$Cl$_2$, solvent B: EtOAc. Gradient: 0% B to 40% B in 25 minutes to give 0.006 g of Example 3 as a white solid.

99% at 2.7 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 415.16 [M−H]$^-$.

Example 4

4-((1R,2R,6R,7S)-2-methyl-3,3-dioxido-10-oxa-3-thia-4-azatricyclo[5.2.1.0$^{2,6}$]dec-8-en-4-yl)-2-(trifluoromethyl)benzonitrile

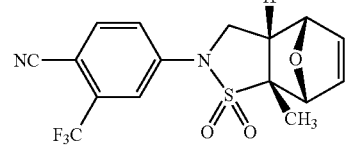

Example 4 was prepared from Example 2ii by the general procedure described for Example 3.

99% at 2.7 min (retention times) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 415.16 [M−H]$^+$.

Examples 5i and 5ii 4-((1S,2R,6R,7R)-3,3-dioxido-10-oxa-3-thia-4-aza-tricyclo[5.2.1.0$^{2,6}$]dec-8-en-4-yl)-2-(trifluoromethyl)benzonitrile (5i) and 4-((1R,2S,6S,7S)-3,3-dioxido-10-oxa-3-thia-4-aza-tricyclo[5.2.1.0$^{2,6}$]dec-8-en-4-yl)-2-(trifluoromethyl)benzonitrile (5ii)

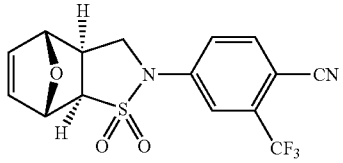

(5i)

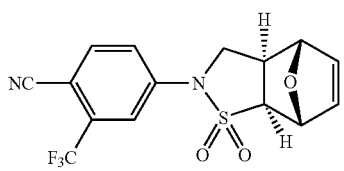

(5ii)

The racemic mixture Example 1ii was separated into individual antipodes by use of a Chiralpack AD column (250×4.6 mm, 10 um), flow rate: 2.0 mL/min, Detector wavelength: 220 nm. Mobile Phase:CO2/MeOH-ACN (50/50). Example 5I was eluted at 5.3 minutes and Example 5ii was eluted at 6.9 minutes. Absolute stereochemistry is as drawn and was determined by single crystal X-ray analysis of Example 5i.

Example 5i: 96% at 2.57 min (retention time) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 415.16 [M−H]$^−$.

Example 5ii: 99% at 2.57 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 415.16 [M−H]$^−$.

Example 6

4-((1S,2R,6R,7R)-3,3-dioxido-10-oxa-3-thia-4-aza-tricyclo[5.2.1.0$^{2,6}$]dec-4-yl)-2-(trifluoromethyl)benzonitrile

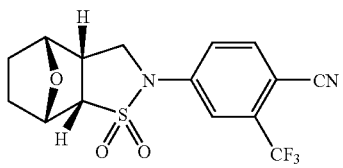 [SMILES: N#Cc1ccc(N2C[C@@H]3[C@@H]([C@@H]4CC[C@H]3O4)S2(=O)=O)cc1C(F)(F)F]

To a solution of Example 2 (0.025 g, 0.070 mmol) in EtOAc (10 mL) was added 10% Pd/C (0.012 g). The reaction mixture was stirred under a H$_2$ balloon at 1 atmosphere for 2 hours. Next, the reaction mixture was filtered through celite and the filtrate was concentrated in vacuo to give 0.025 g of Example 6 as a white solid in 93% yield.

99% at 2.88 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 417.16 [M−H]$^−$.

Example 7

4-((1R,2S,6S,7S)-3,3-dioxido-10-oxa-3-thia-4-aza-tricyclo[5.2.1.0$^{2,6}$]dec-4-yl)-2-(trifluoromethyl)benzonitrile

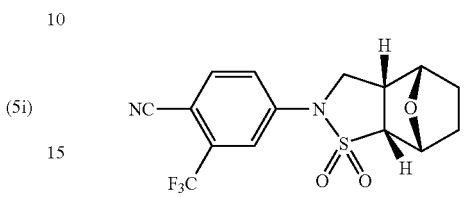

Example 7 was prepared from Example 2ii by the general method described in Example 6.

99% at 2.88 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 417.16 [M−H]$^−$.

Example 8

4-((4 1S,2R,6R,7S,8S,10S)-3,3-dioxido-9,11-dioxa-3-thia-4-azatetracyclo[5.3.1.0$^{2,6}$.0$^{8,10}$]undec-4-yl)-2-(trifluoromethyl)benzonitrile

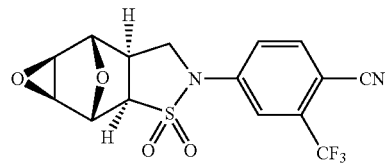 [SMILES: N#Cc1ccc(N2C[C@@H]3[C@@H]4O[C@@H]([C@H]5O[C@H]54)[C@@H]3S2(=O)=O)cc1C(F)(F)F]

To a solution of Example 5i (0.10 g, 0.28 mmol) in CH$_2$Cl$_2$ (5 mL) at 22° C. was added mCPBA (0.32 g, 1.1 mmol). The reaction mixture was stirred at 22° C. under nitrogen for 15 hours. Next, 3-hydroxyl pyridine (0.13 g, 1.4 mmol) was added. The reaction mixture was stirred at 22° C. for 25 min., and then diluted with EtOAc, washed with saturated NaHCO$_3$ (100 mL), brine, dried over MgSO$_4$ and filtered. The filtrate was concentrated in vacuo to give 0.09 g of racemic Example 8 as a white solid in 87% yield.

86% at 2.35 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 431.06 [M−H]$^−$.

Example 9

4((1R,2S,6S,7R,8R,10R)-3,3-dioxido-9,11-dioxa-3-thia-4-azatetracyclo[5.3.1.0$^{2,6}$.0$^{8,10}$]undec-4-yl)-2-(trifluoromethyl)benzonitrile

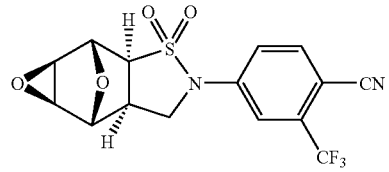 [SMILES: N#Cc1ccc(N2C[C@H]3[C@H]4O[C@H]([C@@H]5O[C@@H]54)[C@H]3S2(=O)=O)cc1C(F)(F)F]

Example 9 was prepared from Example 5ii by the general procedure described in Example 8.

83% at 2.53 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 431.06 [M−H]$^-$.

Examples 10i, 10ii and 10iii rac-4-((1R,2R,6R,7S,9R)-9-hydroxy-3,3-dioxido-10-oxa-3-thia-4-azatricyclo[5.2.1.0$^{2,6}$]dec-4-yl)-2-(trifluoromethyl)benzonitrile (10i)

rac-4-((1R,2R,6R,7R,8S)-8-hydroxy-3,3-dioxido-10-oxa-3-thia-4-azatricyclo[5.2.1.0$^{2,6}$]dec-4-yl)-2-(trifluoromethyl)benzonitrile (10ii) and rac-4-((1R,2R,6R,7R,8R)-8-hydroxy-3,3-dioxido-10-oxa-3-thia-4-azatricyclo [5.2.1.0$^{2,6}$]dec-4-yl)-2-(trifluoromethyl)benzonitrile (10iii)

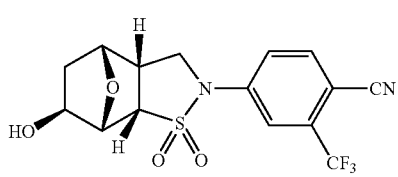
(10i)

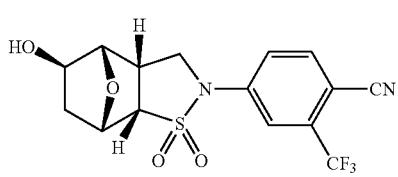
(10ii)

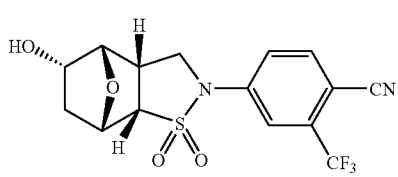
(10iii)

To a solution of Example 2i (0.10, 0.28 mmol) in THF (1.5 mL) at 0° C. was added $BH_3$.THF (1.0 M solution in THF, 1.0 mL, 1.0 mmol) drop-wise. The reaction mixture was stirred at 0° C. for 1.5 hours. Next, phosphate buffer (pH 7.4, 3.0 mL) was added followed by the addition of $H_2O_2$ (30% in $H_2O$, 3.0 mL). The reaction mixture was stirred for 2 hours. Next, the reaction mixture was diluted with EtOAc, the organic layer was separated and stirred with 10% $Na_2SO_3$ (5.0 mL) for 20 min. The organic layer was separated and washed with brine, dried over $MgSO_4$ and filtered. The filtrate was concentrated in vacuo and purified with prep TLC, eluting with 50% EtOAc/$CH_2Cl_2$ to give 0.025 g of Example 10i as a white solid, 0.005 g of Example 10ii as a white solid, and 0.005 g of Example 10iii as a white solid.

Example 10i: 98% at 2.32 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 433.09 [M−H]$^-$.

Example 10ii: 96% at 2.46 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 433.09 [M−H]$^-$.

Example 10iii: 96% at 2.51 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 433.05 [M−H]$^-$.

Example 11

4-((1S,2R,6R,7R)-3,3-dioxido-10-oxa-3-thia-4-azatricyclo[5.2.1.0$^{2,6}$]dec-4-yl)-2-(trifluoromethyl)benzonitrile

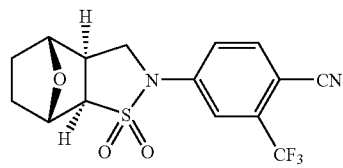 [SMILES: N#Cc1ccc(N2C[C@H]3[C@H]([C@@H]4CC[C@H]3O4)S2(=O)=O)cc1C(F)(F)F]

Example 11 was prepared from Example 5i by the general method described in Example 6.

98% at 2.633 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 417.16 [M−H]$^-$.

Example 12

4-((4R,2S,6S,7S)-3,3-dioxido-10-oxa-3-thia-4-azatricyclo[5.2.1.0$^{2,6}$]dec-4-yl)-2-(trifluoromethyl)benzonitrile

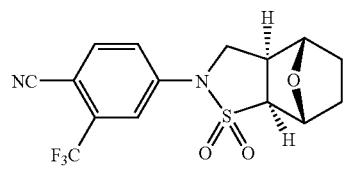

Example 12 was prepared from Example 5ii by the general method described in Example 6.

98% at 2.60 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 417.16 [M−H]$^-$.

Example 13

4-((1S,2R,6R,7R,9S)-9-hydroxy-3,3-dioxido-10-oxa-3-thia-4-azatricyclo[5.2.1.0$^{2,6}$]dec-4-yl)-2-(trifluoromethyl)benzonitrile

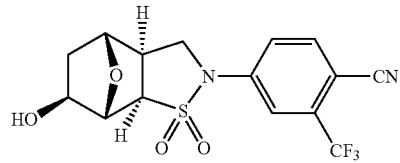 [SMILES: N#Cc1ccc(N2C[C@H]3[C@H]([C@H]4O[C@@H]3C[C@@H]4O)S2(=O)=O)cc1C(F)(F)F]

Example 13 was prepared from Example 5i by the general method described for Example 10. Only one regioisomer was isolated in the reaction.

92% at 2.28 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 433.06 [M−H]⁻.

Example 14

4-((1S,2R,6R,7R,9R)-9-fluoro-3,3-dioxido-10-oxa-3-thia-4-azatricyclo[5.2.1.0$^{2,6}$]dec-4-yl)-2-(trifluoromethyl)benzonitrile

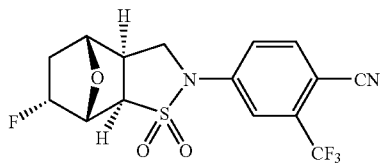 [SMILES: N#Cc1ccc(N2C[C@H]3[C@H]([C@H]4O[C@@H]3C[C@H]4F)S2(=O)=O)cc1C(F)(F)F]

Diethylamino sulfur trifluoride (0.035 mL, 0.26 mmol) was added slowly to a solution of Example 13 (0.014 g, 0.037 mmol) in $CH_2Cl_2$ (0.5 mL) at 22° C. The reaction mixture was stirred at 22° C. under nitrogen for 15 hours, and then purified by reverse phase preparative TLC plate, eluting with 20% $EtOAc/CH_2Cl_2$ to give 0.006 g of Example 14 as a white solid in 43% yield.

98% at 2.77 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 435.13 [M−H]⁻.

Example 15

4-((1R,2S,6S,7S,9R)-9-hydroxy-3,3-dioxido-10-oxa-3-thia-4-azatricyclo[5.2.1.0$^{2,6}$]dec-4-yl)-2-(trifluoromethyl)benzonitrile

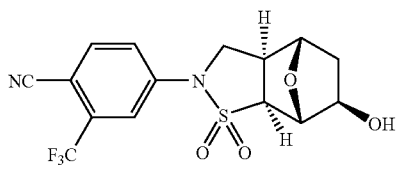

Example 15 was prepared from Example 5ii by the general method described in Example 10.

95% at 2.30 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 433.06 [M−H]⁻.

Example 16

4-((1R,2S,6S,7S,9S)-9-fluoro-3,3-dioxido-10-oxa-3-thia-4-azatricyclo[5.2.1.0$^{2,6}$]dec-4-yl)-2-(trifluoromethyl)benzonitrile

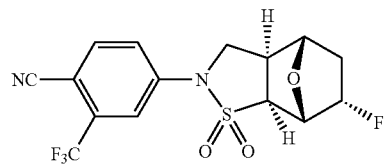

Example 16 was prepared from Example 15 by the general method described in Example 14.

98% at 2.77 min (retention time) (YMC ODS-A column 4.6×50 mm eluting with 10-90% aqueous methanol over 4 minutes containing 0.1% $H_3PO_4$, 4 mL/min, monitoring at 220 nm). MS (ES): m/z 435.08 [M−H]⁻.

Example 17 rac-4-((1R,2R,6R,7S)-1,7-dimethyl-3,3-dioxido-10-oxa-3-thia-4-azatricyclo[5.2.1.0$^{2,6}$]dec-8-en-4-yl)-2-(trifluoromethyl)benzonitrile

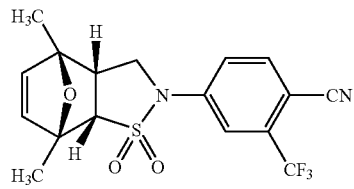 [SMILES: C[C@]12CC[C@](C)(O1)[C@@H]1[C@H]2CN(c2ccc(C#N)c(C(F)(F)F)c2)S1(=O)=O]

Step A: rac-4-((1S,2S,6R,7R)-1,7-dimethyl-3,3-dioxido-5-oxo-10-oxa-3-thia-4-azatricyclo[5.2.1.0$^{2,6}$]dec-8-en-4-yl)-2-(trifluoromethyl)benzonitrile (17A)

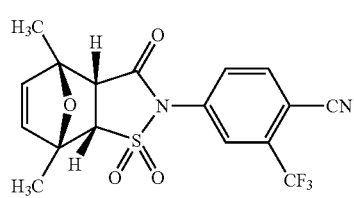

To a suspension of Compound 1D (1.0 g, 3.3 mmol) in $CH_2Cl_2$ (3 mL) at 22° C. was added 2,5-dimethyl furan (1.4 mL, 13.2 mmol). The reaction mixture was stirred at 22° C. for 30 minutes and then concentrated in vacuo to give 1.31 g of racemic Compound 17A as a single isomer and an off-white solid.

98% at 3.2 min (retention time) (YMC ODS-A column 4.6×50 mm eluting with 10-90% aqueous methanol over 4 minutes containing 0.1% H₃PO₄, 4 mL/min, monitoring at 220 nm). MS (ES): m/z 457.19 [M–H+OAc]⁻.

Step B: rac-(1S,2S,3S,4R)—N-(4-cyano-3-(trifluoromethyl)phenyl)-3-(hydroxymethyl)-1,4-dimethyl-7-oxabicyclo[2.2.1]hept-5-ene-2-sulfonamide

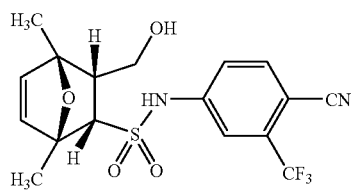

(17B)

To a solution of Compound 17A (1.3 g, 3.27 mmol) in tetrahydrofuran (THF, 5 mL) and methanol (5 mL) at 22° C. was added NaBH₄ (0.5 g, 13.2 mmol). The resulting reaction mixture was stirred for 30 minutes, and then acidified by the addition of saturated NH₄Cl solution (250 mL) and extracted with CH₂Cl₂ (3×250 mL). The organic phases were combined, dried over anhydrous sodium sulfate, and filtered. The filtrate was concentrated in vacuo to give the crude ring opened alcohol-sulfonamide Compound 1782B (1.3 g) as a white solid.

98% at 3.00 min (retention time) (YMC ODS-A column 4 6×50 mm eluting with 10-90% aqueous methanol over 4 minutes containing 0.1% H₃PO₄, 4 mL/min, monitoring at 220 nm). MS (ES): m/z 461.09[M–H+OAc]⁻.

Step C: rac-4-((1R,2R,6R,7S)-1,7-dimethyl-3,3-dioxido-10-oxa-3-thia-4-azatricyclo[5.2.1.0²,⁶]dec-8-en-4-yl)-2-(trifluoromethyl)benzonitrile

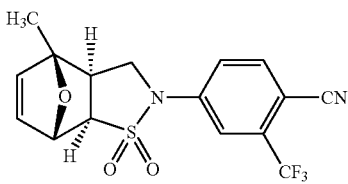 [SMILES: C[C@]12C=C[C@H](O1)[C@H]1[C@@H]2CN(c2ccc(C#N)c(C(F)(F)F)c2)S1(=O)=O]

To a solution of Compound 17B (1.30 g, 3.23 mmol) in tetrahydrofuran (THF, 5 mL) was added triphenyl phosphine (1.28 g, 4.88 mmol) followed by diisopropyl azodicarboxylate (0.96 mL, 4.88 mmol). The reaction mixture was stirred at 22° C. under nitrogen for 1 hour, and then concentrated in vacuo to give a crude material which was purified with flash chromatography in ISCO using 80 g column, Flow rate: 60 mL/min, solvent A: dichloromethane, solvent B: EtOAc. Gradient: 0% B to 20% B in 25 minutes to give 1.0 g of racemic Example 17 as a white solid in 78% yield.

99% at 3.14 min (retention time) (YMC ODS-A column 4 6×50 mm eluting with 10-90% aqueous methanol over 4 minutes containing 0.1% H₃PO₄, 4 mL/min, monitoring at 220 nm). MS (ES): m/z 443.17 [M–H+OAc]⁻.

Example 18 rac-4-((1R,2R,6R,7S)-1,7-dimethyl-3,3-dioxido-10-oxa-3-thia-4-azatricyclo[5.2.1.0²,⁶]dec-4-yl)-2-(trifluoromethyl)benzonitrile

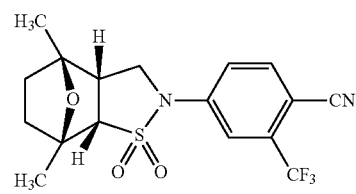

Example 18 was prepared as a racemate from Example 17 by the general method described in Example 6.

98% at 3.0 min (retention time) (YMC ODS-A column 4 6×50 mm eluting with 10-90% aqueous methanol over 4 minutes containing 0.1% H₃PO₄, 4 mL/min, monitoring at 220 nm). MS (ES): m/z 461.17 [M–H]⁻.

Example 19 rac-4-((1R,2R,6R,7S)-7-methyl-3,3-dioxido-10-oxa-3-thia-4-azatricyclo[5.2.1.0²,⁶]dec-8-en-4-yl)-2-(trifluoromethyl)benzonitrile

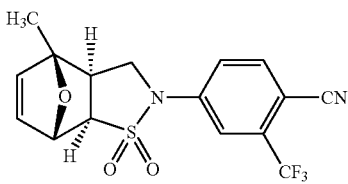 [SMILES: C[C@]12C=C[C@H](O1)[C@H]1[C@@H]2CN(c2ccc(C#N)c(C(F)(F)F)c2)S1(=O)=O]

Step A: rac-4-((1S,2R,6S,7R)-7-methyl-3,3-dioxido-5-oxo-10-oxa-3-thia-4-azatricyclo[5.2.1.0²,⁶]dec-8-en-4-yl)-2-(trifluoromethyl)benzonitrile

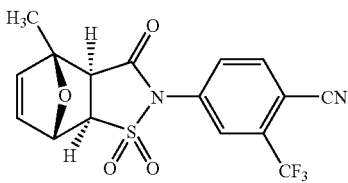

(19A)

To a suspension of Compound 1D (1.0 g, 3.3 mmol) in CH₂Cl₂ (3 mL) at 22° C. was added 2-methyl furan (3.0 mL, 32.8 mmol). The reaction mixture was stirred at 22° C. for 30 minutes. The solid material was isolated by filtration to give 0.83 g of racemic Compound 19A as an off-white solid.

98% at 2.8 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 443.18 [M−H+OAc]⁻.

Step B: rac-(1S,2R,3R,4R)—N-(4-cyano-3-(trifluoromethyl)phenyl)-3-(hydroxymethyl)-4-methyl-7-oxabicyclo[2.2.1]hept-5-ene-2-sulfonamide

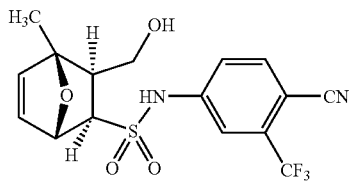

(19B)

To a solution of Compound 19A (1.60 g, 4.20 mmol) in tetrahydrofuran (THF, 10 mL) and methanol (10 mL) at 22° C. was added $NaBH_4$ (0.63 g, 16.7 mmol). The resulting reaction mixture was stirred for 30 minutes, acidified by addition of saturated $NH_4Cl$ solution (100 mL), and extracted with $CH_2Cl_2$ (3×150 mL). The organic phases were combined, dried over anhydrous sodium sulfate and filtered. The filtrate was concentrated in vacuo to give 1.6 g of Compound 19B as a white solid.

95% at 2.65 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 387.13[M−H]⁻.

Step C

To a solution of Compound 19B (1.60 g, 4.12 mmol) in THF (5 mL) was added triphenyl phosphine (1.60 g, 6.19 mmol) followed by diisopropyl azodicarboxylate (1.2 mL, 6.19 mmol). The reaction mixture was stirred at 22° C. under nitrogen for 1 hour. Then it was concentrated in vacuo to give a crude material, which was purified with flash chromatography in ISCO using 120 g column, Flow rate: 85 mL/min, solvent A: dichloromethane, solvent B: EtOAc. Gradient: 0% B to 20% B in 25 minutes to give 0.88 g of racemic Example 19 as a white solid in 59% yield.

99% at 2.7 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 371.28 [M+H]⁺.

Example 20 rac-4-((1R,2R,6R,7S)-7-methyl-3,3-dioxido-10-oxa-3-thia-4-azatricyclo[5.2.1.0²,⁶]dec-8-en-4-yl)-2-(trifluoromethyl)benzonitrile

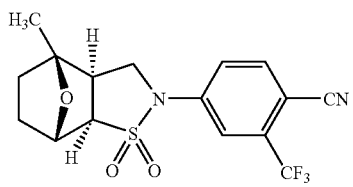

To a solution of Example 19 (0.053 g, 0.14 mmol) in EtOAc (15 mL) was added 10% Pd/C (0.025 g). The reaction mixture was stirred under a hydrogen balloon at 1 atmosphere for 1.5 hours and filtered through celite. The filtrate was concentrated in vacuo to give 0.045 g of racemic Example 20 as a white solid in 85% yield.

98% at 2.76 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 431.09 [M−H+OAc]⁻.

Examples 21i and 21ii rac-4-((1R,2R,6R,7S)-7-methyl-3,3-dioxido-10-oxa-3-thia-4-azatricyclo[5.2.1.0²,⁶]dec-8-en-4-yl)-2-(trifluoromethyl)benzonitrile (21i) and rac-4-((1R,2R,6R,7S)-1-methyl-3,3-dioxido-10-oxa-3-thia-4-azatricyclo[5.2.1.0²,⁶]dec-8-en-4-yl)-2-(trifluoromethyl)benzonitrile (21ii)

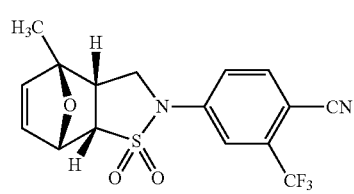

(21i)

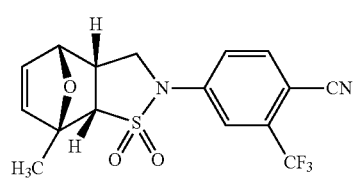

(21ii)

Step A: rac-4-((1S,2S,6R,7R)-7-methyl-3,3-dioxido-5-oxo-10-oxa-3-thia-4-azatricyclo[5.2.1.0²,⁶]dec-8-en-4-yl)-2-(trifluoromethyl)benzonitrile

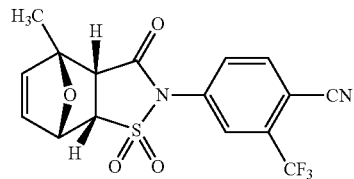

(21A)

To a suspension of Compound 1D (1.0 g, 3.3 mmol) in $CH_2Cl_2$ (3 mL) at 22° C. was added 2-methyl furan (3.0 mL, 32.8 mmol). The reaction mixture was stirred at 22° C. for 30 min. Then the solid was isolated by filtration to give 0.83 g of Compound 21A as an off-white solid. The filtrate was concentrated to give 0.43 g of a racemic mixture of regioisomers as a yellow solid.

98% at 2.9 min (retention time) (YMC ODS-A column 4 6×50 mm eluting with 10-90% aqueous methanol over 4 minutes containing 0.1% $H_3PO_4$, 4 mL/min, monitoring at 220 nm). MS (ES): m/z 443.18 [M−H+OAc]⁻.

Step B

To a solution a mixture of Compound 21A (0.37 g, 0.97 mmol) in tetrahydrofuran (THF, 10 mL) and methanol (10 mL) at 22° C. was added NaBH$_4$ (0.15 g, 3.9 mmol). The resulting reaction mixture was stirred for 30 minutes, then acidified by the addition of saturated NH$_4$Cl solution (50 mL) and extracted with CH$_2$Cl$_2$ (3×50 mL). The organic phases were combined, dried over anhydrous sodium sulfate and filtered. The filtrate was concentrated in vacuo to give the crude mixture of alcohols (0.37 g) as a white solid. The alcohols were then dissolved in THF (5 mL), and triphenyl phosphine (0.38 g, 1.50 mmol) was added followed by diisopropyl azodicarboxylate (0.30 mL, 1.50 mmol). The reaction mixture was stirred at 22° C. under nitrogen for 10 minutes, and then concentrated in vacuo to give a crude material which was purified by flash chromatography using an ISCO system with a 120 g column, Flow rate: 85 mL/min, solvent A: dichloromethane, solvent B: EtOAc. Gradient: 0% B to 20% B in 25 minutes to give 0.17 g of racemic Example 21i as a white solid and 0.058 g of racemic Example 21ii as white solid in total 64% yield.

Example 21i: 99% at 2.86 min (retention time) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 429.15 [M+H-OAc]$^-$.

Example 21ii: 99% at 3.06 min (retention time) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 429.15 [M+H-OAc]$^-$.

Example 22 rac-4-((1R,2R,6R,7S)-7-methyl-3,3-dioxido-10-oxa-3-thia-4-azatricyclo[5.2.1.0$^{2,6}$]dec-4-yl)-2-(trifluoromethyl)benzonitrile

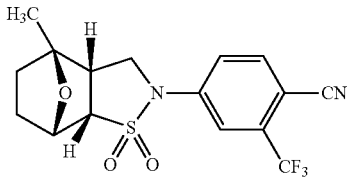 [SMILES: C[C@]12CC[C@H](O1)[C@@H]1[C@H]2CN(c2ccc(C#N)c(C(F)(F)F)c2)S1(=O)=O]

To a solution of Example 21i (0.030 g, 0.081 mmol) in EtOAc (15 mL) was added 10% Pd/C (0.015 g). The reaction mixture was stirred under a hydrogen balloon at 1 atmosphere for 1.5 hours. Next, the reaction mixture was filtered through celite. The filtrate was concentrated in vacuo to give 0.028 g of racemic Example 22 as a white solid in 93% yield.

98% at 3.028 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 431.23 [M−H+OAc]$^-$.

Example 23 rac-4-((1R,2R,6R,7S)-1-methyl-3,3-dioxido-10-oxa-3-thia-4-azatricyclo[5.2.1.0$^{2,6}$]dec-4-yl)-2-(trifluoromethyl)benzonitrile

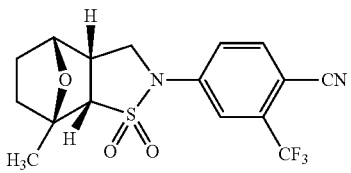 [SMILES: C[C@@]12CC[C@@H](O1)[C@@H]1CN(c3ccc(C#N)c(C(F)(F)F)c3)S(=O)(=O)[C@@H]12]

To a solution of Example 21ii (0.015 g, 0.040 mmol) in EtOAc (15 mL) was added 10% Pd/C (0.007 g). The reaction mixture was stirred under a hydrogen balloon at 1 atmosphere for 2 hours. The reaction mixture was filtered through celite and the filtrate was concentrated in vacuo to give 0.015 g of racemic Example 23 as a white solid in 98% yield.

98% at 3.13 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 431.21 [M−H+OAc]$^-$.

Examples 24i and 24ii rac-4-((1R,2R,6R,7R,8S)-8-azido-3,3-dioxido-10-oxa-3-thia-4-azatricyclo[5.2.1.0$^{2,6}$]dec-4-yl)-2-(trifluoromethyl)benzonitrile (24i) and rac-4-((1R,2R,6R,7S,9R)-9-azido-3,3-dioxido-10-oxa-3-thia-4-azatricyclo[5.2.1.0$^{2,6}$]dec-4-yl)-2-(trifluoromethyl)benzonitrile (24ii)

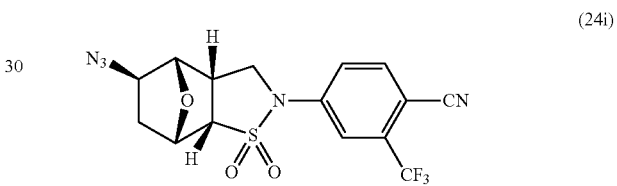

(24i)

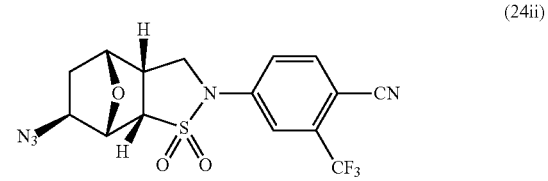

(24ii)

To a solution of NaN$_3$ (91 mg, 1.4 mmol) in a mixed solvent of THF (2 ml) and H$_2$O (1 mL) was added Hg(OAc)$_2$ (107 mg, 0.34 mmol), followed by the addition of Example 1i (100 mg, 0.28 mmol). The reaction mixture was stirred at room temperature for 2.5h. Then 15% aqueous KOH (1 mL) was added followed by the dropwise addition of a solution of NaBH$_4$(30 mg, 0.79 mmol) in 15% aqueous KOH (1 mL). The mixture was stirred at room temperature for 2 h. The organic phase was separated and the aqueous was extracted with EtOAc for two times. The combined extracts were washed with brine, dried over Na$_2$SO$_4$, concentrated to give a mixture of Examples 24i and 24ii as a colorless sticky oil.
RT=2.76 min (Chromolith SpeedROD 4.6×50 mm eluting with 10-90% aqueous methanol over 4 minutes containing 0.1% TFA, 4 mL/min, monitoring at 220 nm). MS (ES): m/z 398 [M−H$^+$]$^−$.

Examples 25i and 25ii rac-4-((1R,2R,6R,7R,8S)-8-amino-3,3-dioxido-10-oxa-3-thia-4-azatricyclo[5.2.1.0$^{2,6}$]dec-4-yl)-2-(trifluoromethyl)benzonitrile (25i) and rac-4-((1R,2R,6R,7S,9R)-9-amino-3,3-dioxido-10-oxa-3-thia-4-azatricyclo[5.2.1.0$^{2,6}$]dec-4-yl)-2-(trifluoromethyl)benzonitrile (25ii)

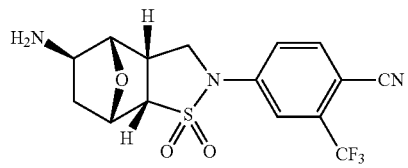

(25i)

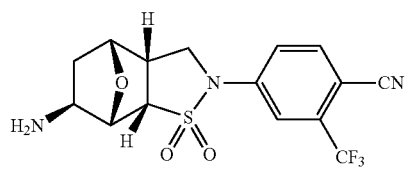

(25ii)

The mixture of Examples 24i and 24ii was dissolved in a mixed solvent of THF (3 mL) and H$_2$O (0.25 mL). To the mixture, PPh$_3$ (147 mg, 0.56 mmol) was added. The mixture was stirred at 70° C. for 2 h, and then cooled down. The reaction mixture was purified by SCX cartridge to give a mixture of Examples 25i and 25ii.
Example 25i: RT=1.488 min (Chromolith SpeedROD 4.6×50 mm eluting with 10-90% aqueous methanol over 4 minutes containing 0.1% TFA, 4 mL/min, monitoring at 220 nm). MS (ES): m/z 374 [M+H$^+$]$^−$.
Example 25ii: RT=1.675 min (Chromolith SpeedROD 4.6×50 mm eluting with 10-90% aqueous methanol over 4 minutes containing 0.1% TFA, 4 mL/min, monitoring at 220 nm). MS (ES): m/z 374 [M+H$^+$]$^−$.

Examples 26i and 26ii methyl rac-((1R,2R,6R,7R,8S)-4-(4-cyano-3-(trifluoromethyl)phenyl)-3,3-dioxido-10-oxa-3-thia-4-azatricyclo[5.2.1.0$^{2,6}$]dec-8-yl)carbamate (26i) and
methyl rac-((1R,2R,6R,7S,9R)-4-(4-cyano-3-(trifluoromethyl)phenyl)-3,3-dioxido-10-oxa-3-thia-4-azatricyclo[5.2.1.0$^{2,6}$]dec-9-yl)carbamate (26ii)

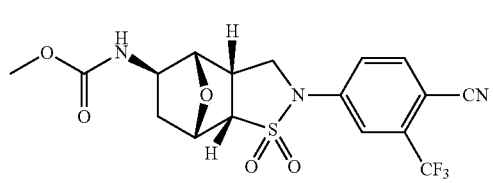

(26i)

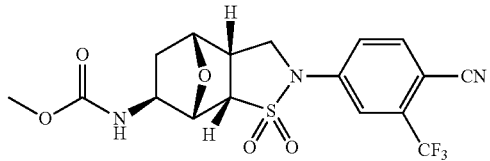

(26ii)

To a solution of a mixture of Examples 25i and 25ii in THF (3 mL) was added TEA (117 μL, 0.84 mmol). The mixture was cooled to 0° C. and methyl chloroformate (65 μL, 0.84 mmol) was added slowly. Some solid precipitated. HPLC shows some starting material remained. Saturated aqueous NaHCO$_3$ solution (1 mL) was added, followed by methyl chloroformate (65 μL, 0.84 mmol). The reaction mixture was stirred for 30 min. The organic layer was separated and the aqueous layer was extracted with EtOAc. The combined extracts were concentrated, purified by prep HPLC to afford Example 26i (10.0 mg, 8% for 3 steps) and Example 26ii (56.9 mg, 47% for 3 steps) as a white solids.
Example 26i: RT=2.408 min (Chromolith SpeedROD 4.6×50 mm eluting with 10-90% aqueous methanol over 4 minutes containing 0.1% TFA, 4 mL/min, monitoring at 220 nm). MS (ES): m/z 430 [M−H$^+$]$^−$.
Example 26ii: RT=2.142 min (Chromolith SpeedROD 4.6×50 mm eluting with 10-90% aqueous methanol over 4 minutes containing 0.1% TFA, 4 mL/min, monitoring at 220 nm). MS (ES): m/z 432 [M+H$^+$].

Example 27 benzyl (1S,2S,6S,7R)-4-(4-cyano-3-(trifluoromethyl)phenyl)-10-oxa-3-thia-4-azatricyclo[5.2.1.0$^{2,6}$]decane-2-carboxylate 3,3-dioxide To a solution of Example 6 (81 mg, 0.226 mmol) in THF (6 ml) at 0° C. was added benzylchloroformate (60 μl, 0.43 mmol), followed by the slow addition of 1.0M LiHDMS (0.60 ml, 0.6 mmol). The reaction mixture was stirred at 0° C. for 20 min, and then quenched with saturated aqueous NH$_4$Cl and extracted with EtOAc for 2 times. The combined extracts were washed with brine, dried over Na$_2$SO$_4$, concentrated and purified with flash chromatography to give Example 27 (116 mg, 105%).

RT=3.368 min (Chromolith SpeedROD 4.6×50 mm eluting with 10-90% aqueous methanol over 4 minutes containing 0.1% TFA, 4 mL/min, monitoring at 220 nm). MS (ES): m/z 551 [M+OAc]⁻.

Example 28

(1S,2S,6S,7R)-4-(4-cyano-3-(trifluoromethyl)phenyl)-10-oxa-3-thia-4-azatricyclo[5.2.1.0$^{2,6}$]decane-2-carboxylic acid 3,3-dioxide

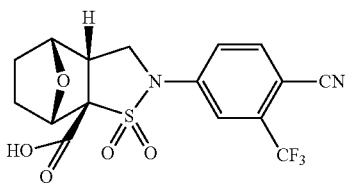 [SMILES: N#Cc1ccc(N2C[C@H]3[C@H]4CC[C@H](O4)[C@@]3(C(=O)O)S2(=O)=O)cc1C(F)(F)F]

To a solution of Example 27 (116 mg, 0.235 mmol) in EtOAc (10 mL) was added Degussa catalyst (60 mg). The mixture was shaken under 40 psi hydrogen for 2 h. The catalyst was filtered off, and the filtrate was concentrated, stripped with toluene for 3 times, and dried in vacuo to give Example 28 (160 mg) as a yellow solid.

RT=2.490 min (Chromolith SpeedROD 4.6×50 mm eluting with 10-90% aqueous methanol over 4 minutes containing 0.1% TFA, 4 mL/min, monitoring at 220 nm). MS (ES): m/z 357 [M-CO2-H]⁻.

Example 29

(1S,2S,6S,7R)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide

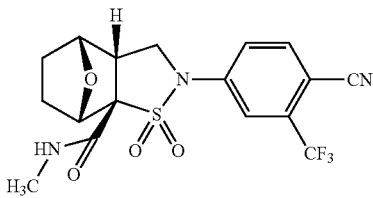 [SMILES: CNC(=O)[C@@]12[C@@H]3CC[C@@H](O3)[C@@H]1CN(c1ccc(C#N)c(C(F)(F)F)c1)S2(=O)=O]

To a suspension of Example 28 (61 mg, 0.152 mmol) in dry DCM (3 mL) was added (COCl)₂ (150 µL, 1.72 mmol), followed by 1 drop of DMF. The mixture was stirred for 1 h. Next, the reaction mixture was concentrated and the residue was stripped with dry DCM twice and dried in vacuo. The resulting solid was dissolved in dry DCM (3 ml) and 2.0M MeNH₂ in THF (1.5 ml) was added, followed by 3 drops of Et₃N. The reaction mixture was stirred at room temperature overnight. The reaction mixture was concentrated and purified by prep HPLC to give Example 29 (22.7 mg, 61% for two steps) as a white solid.

RT=2.242 min (Chromolith SpeedROD 4.6×50 mm eluting with 10-90% aqueous methanol over 4 minutes containing 0.1% TFA, 4 mL/min, monitoring at 220 nm). MS (ES): m/z 416 [M+H]⁺.

Example 30 benzyl (1R,2R,6R,7S)-4-(4-cyano-3-(trifluoromethyl)phenyl)-10-oxa-3-thia-4-azatricyclo[5.2.1.0$^{2,6}$]decane-2-carboxylate 3,3-dioxide

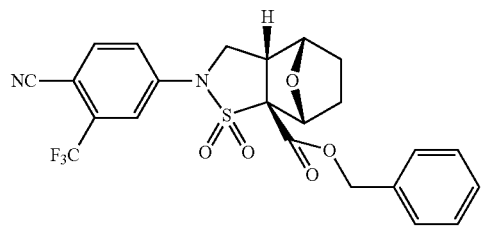 [SMILES: N#Cc1ccc(N2C[C@@H]3[C@@H]4CC[C@@H](O4)[C@]3(C(=O)OCc3ccccc3)S2(=O)=O)cc1C(F)(F)F]

Example 30 was prepared from Example 7 by the general method described in Example 27.

RT=3.335 min (Chromolith SpeedROD 4.6×50 mm eluting with 10-90% aqueous methanol over 4 minutes containing 0.1% TFA, 4 mL/min, monitoring at 220 nm). MS (ES): m/z 551 [M+OAc]⁻.

Example 31

(1R,2R,6R,7S)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide

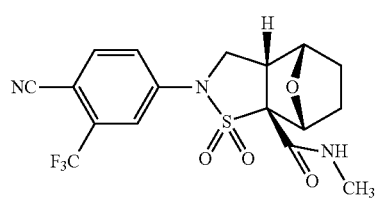 [SMILES: CNC(=O)[C@]12[C@H](CN(c3ccc(C#N)c(C(F)(F)F)c3)S1(=O)=O)[C@@H]1CC[C@H]2O1]

Example 31 was prepared from Example 7 by the general method described in Example 29.

RT=2.220 min (Chromolith SpeedROD 4.6×50 mm eluting with 10-90% aqueous methanol over 4 minutes containing 0.1% TFA, 4 mL/min, monitoring at 220 nm). MS (ES): m/z 416 [M+H]⁺.

Example 32 rac-4-((1R,2S,6S,7S)-3,3-dioxido-10-oxa-3-thia-4-azatricyclo[5.2.1.0$^{2,6}$]dec-4-yl)-2-(trifluoromethyl)benzonitrile

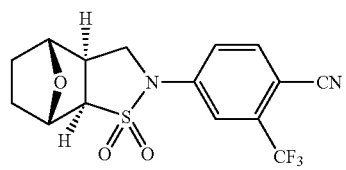

Racemic Example 32 was prepared from Example 1ii by the general method described in Example 6.

RT=2.243 min (Chromolith SpeedROD 4.6×50 mm eluting with 10-90% aqueous methanol over 4 minutes containing 0.1% TFA, 4 mL/min, monitoring at 220 nm). MS (ES): m/z 417 [M−H]⁻.

Example 33 rac-(1R,2S,6S,7S)-4-(4-cyano-3-(trifluoromethyl)phenyl)-N-methyl-10-oxa-3-thia-4-azatricyclo[5.2.1.0²,⁶]decane-2-carboxamide 3,3-dioxide

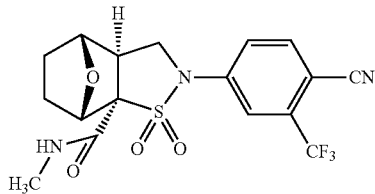 [SMILES: CNC(=O)[C@]12[C@@H]3CC[C@@H](O3)[C@H]1CN(c1ccc(C#N)c(C(F)(F)F)c1)S2(=O)=O]

Example 33 was prepared from Example 32 by the general method described in Examples 27, 28 and 29.

RT=2.080 min (Chromolith SpeedROD 4.6×50 mm eluting with 10-90% aqueous methanol over 4 minutes containing 0.1% TFA, 4 mL/min, monitoring at 220 nm). MS (ES): m/z 414 [M−H]⁻.

Examples 34i, 34ii, 34iii and 34iv rac-4-((1R,2S,6S,7R,8S)-8-hydroxy-3,3-dioxido-10-oxa-3-thia-4-azatricyclo[5.2.1.0²,⁶]dec-4-yl)-2-(trifluoromethyl)benzonitrile (34i)

rac-4-((1R,2S,6S,7S,9R)-9-hydroxy-3,3-dioxido-10-oxa-3-thia-4-azatricyclo[5.2.1.0²,⁶]dec-4-yl)-2-(trifluoromethyl)benzonitrile (34ii)

rac-4-((1R,2S,6S,7R,8R)-8-hydroxy-3,3-dioxido-10-oxa-3-thia-4-azatricyclo[5.2.1.0²,⁶]dec-4-yl)-2-(trifluoromethyl)benzonitrile (34iii) and rac-4-((1R,2S,6S,7S,9S)-9-hydroxy-3,3-dioxido-10-oxa-3-thia-4-azatricyclo[5.2.1.0²,⁶]dec-4-yl)-2-(trifluoromethyl)benzonitrile (34iv)

(34i)
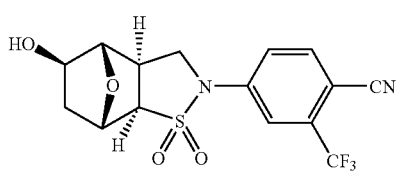

(34ii)
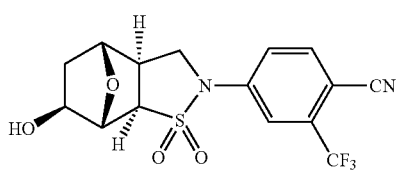

(34iii)
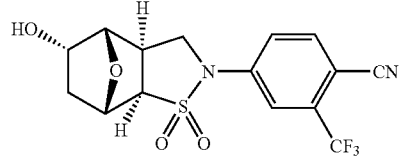

(34iv)
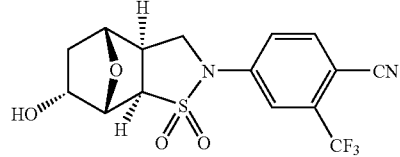

Example 2ii (3.6 g, 10.1 mmol) was subjected to hydroboration by the general method described in Example 10. After flash chromatography (EtOAc/DCM=0-100%), Examples 34i and 34ii were obtained as a mixture (1.14 g, 30%). RT=1.835 min (Chromolith SpeedROD 4.6×50 mm eluting with 10-90% aqueous methanol over 4 minutes containing 0.1% TFA, 4 mL/min, monitoring at 220 nm). MS (ES): m/z 375 [M+H]⁺. Examples 34iii and 34iv were also obtained as a mixture (100 mg, 2.6%). RT=2.100 min (Chromolith SpeedROD 4.6×50 mm eluting with 10-90% aqueous methanol over 4 minutes containing 0.1% TFA, 4 mL/min, monitoring at 220 nm). MS (ES): m/z 375 [M+H]⁺.

Further purification of mixture of Examples 34iii and 34iv with ISCO flash chromatography (acetone/DCM=0-20%) to give Example 34iii (15 mg, lower spot) and Example 34iv (17 mg, higher spot).

Examples 35i and 35ii rac-4-((1R,2S,6S,7R,8R)-8-fluoro-3,3-dioxido-10-oxa-3-thia-4-azatricyclo[5.2.1.0²,⁶]dec-4-yl)-2-(trifluoromethyl)benzonitrile (35i) and rac-4-((1R,2S,6S,7S,9S)-9-fluoro-3,3-dioxido-10-oxa-3-thia-4-azatricyclo[5.2.1.0²,⁶]dec-4-yl)-2-(trifluoromethyl)benzonitrile (35ii)

(35i)
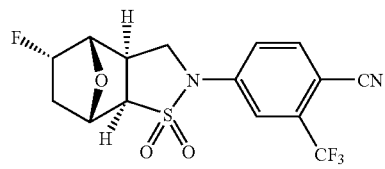

(35ii)
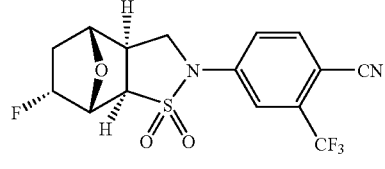

To a solution of Example 34i and Example 34ii (30 mg, 0.08 mmol) in DCM (3 mL) at 0° C. was added DAST (75 μL, 0.57 mmol). The reaction mixture was then stirred at room temperature overnight. The reaction mixture was concentrated and purified by ISCO flash chromatography (EtOAc/hexane=30-100%) to give racemic Example 35i (2.7 mg, 9%) and Example 35ii (4.0 mg, 13%).

Example 35i: RT=2.278 min (Chromolith SpeedROD 4.6× 50 mm eluting with 10-90% aqueous methanol over 4 minutes containing 0.1% TFA, 4 mL/min, monitoring at 220 nm). MS (ES): m/z 435 [M+OAc]⁻.

Example 35ii: RT=2.413 min (Chromolith SpeedROD 4.6×50 mm eluting with 10-90% aqueous methanol over 4 minutes containing 0.1% TFA, 4 mL/min, monitoring at 220 nm). MS (ES): m/z 435 [M+OAc]⁻.

Examples 36i and 36ii 4-((1S,2R,6R,7S,8S)-8-fluoro-3,3-dioxido-10-oxa-3-thia-4-azatricyclo[5.2.1.0$^{2,6}$]dec-4-yl)-2-(trifluoromethyl)benzonitrile (36i) and 4-((1R,2S,6S,7R,8R)-8-fluoro-3,3-dioxido-10-oxa-3-thia-4-azatricyclo[5.2.1.0$^{2,6}$]dec-4-yl)-2-(trifluoromethyl)benzonitrile (36ii)

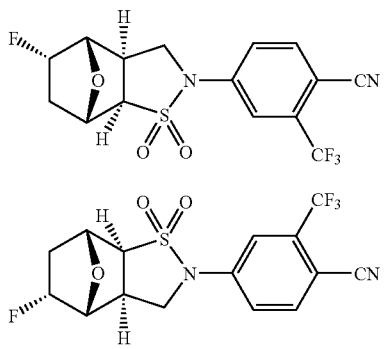

The racemic mixture Example 35i was separated into individual antipodes by use of a Chiralpack AD 250×4.6 mm, 10 μm), flow rate: 1.5 mL/min, detector wavelength: 220 nm. Mobil phase hexanes/MeOH/IPA/DEA=40:30:30:0.1.

Example 36i had a retention time of 7 5 min and Example 36ii was eluted at 14.2 min. All spectral data was identical to that for the racemic mixture. Although the nomenclature and structure indicate a single enantiomer of known absolute stereochemistry, the absolute stereochemistry is unknown and these structures do not represent the absolute stereochemistry.

Examples 37i and 37ii 4-((1S,2R,6R,7S,8S)-8-hydroxy-3,3-dioxido-10-oxa-3-thia-4-azatricyclo[5.2.1.0$^{2,6}$]dec-4-yl)-2-(trifluoromethyl)benzonitrile (37i) and 4-((1R,2S,6S,7R,8R)-8-hydroxy-3,3-dioxido-10-oxa-3-thia-4-azatricyclo[5.2.1.0$^{2,6}$]dec-4-yl)-2-(trifluoromethyl)benzonitrile (37ii)

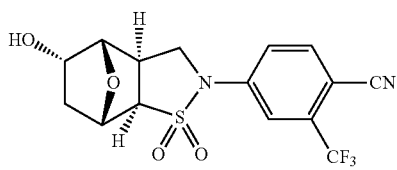

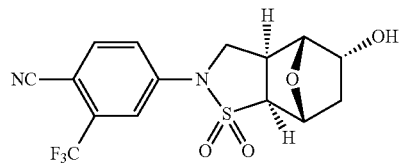

The racemic mixture Example 34iii was separated into individual antipodes by use a Chiralpack AD 250×4.6 mm, 10 μm), flow rate: 1.5 mL/min, detector wavelength: 220 nm. Mobil phase hexanes/MeOH/IPA/DEA=40:30:30:0.1.

Example 37i had a retention time of 7.8 min and Example 37ii was eluted at 15.4 min. All spectral data was identical to that for the racemic mixture. Although the nomenclature and structure indicate a single enantiomer of known absolute stereochemistry, the absolute stereochemistry is unknown and these structures do not represent the absolute stereochemistry.

Examples 38i and 38ii 4-((1S,2R,6R,7R,9R)-9-hydroxy-3,3-dioxido-10-oxa-3-thia-4-azatricyclo[5.2.1.0$^{2,6}$]dec-4-yl)-2-(trifluoromethyl)benzonitrile (38i) and 4-((1R,2S,6S,7S,9S)-9-hydroxy-3,3-dioxido-10-oxa-3-thia-4-azatricyclo[5.2.1.0$^{2,6}$]dec-4-yl)-2-(trifluoromethyl)benzonitrile (38ii)

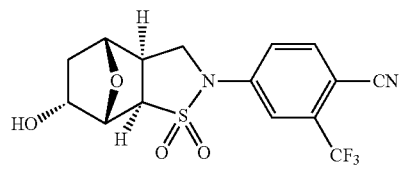

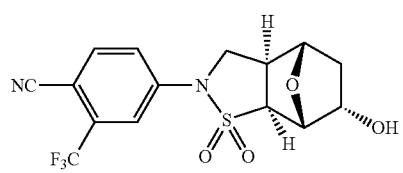

The racemic mixture Example 34iv was separated into individual antipodes by use a Chiralpack AD 250×4.6 mm, 10 μm), flow rate: 1.5 mL/min, detector wavelength: 220 nm. Mobil phase hexanes/MeOH/IPA/DEA=30:35:35:0.1.

Example 38i had a retention time of 6.03 min and Example 38ii was eluted at 11.3 min. All spectral data was identical to that for the racemic mixture. Although the nomenclature and structure indicate a single enantiomer of known absolute stereochemistry, the absolute stereochemistry is unknown and these structures do not represent the absolute stereochemistry.

Examples 39i and 39ii rac-4-((1R,2S,6S,7R,8R)-8-azido-3,3-dioxido-10-oxa-3-thia-4-azatricyclo[5.2.1.0²,⁶]dec-4-yl)-2-(trifluoromethyl)benzonitrile (39i) and rac-4-((1R,2S,6S,7S,9S)-9-azido-3,3-dioxido-10-oxa-3-thia-4-azatricyclo[5.2.1.0²,⁶]dec-4-yl)-2-(trifluoromethyl)benzonitrile (39ii)

(39i)

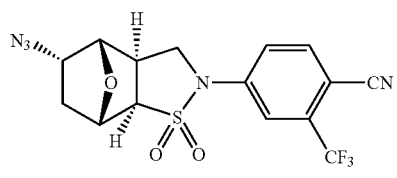

(39ii)

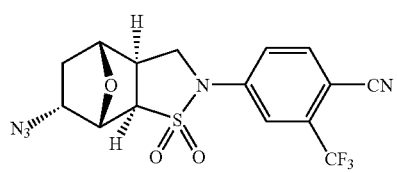

To a suspension of a racemic mixture of Example 34i and Example 34ii (250 mg, 0.668 mmol) in DCM (7 mL) was added pyridine (165 μL, 2.03 mmol) followed by Tf₂O (171 μL, 1.04 mmol). The reaction mixture was stirred for 3.5h. Next, the reaction mixture was diluted with DCM, washed with brine, the organic layer was separated, and the aqueous layer was extracted with EtOAc. The combined organic layers were dried over MgSO₄. Concentrated to give the corresponding triflates as a white solid.

The triflates were dissolved in DMF (3 mL) and NaN₃ (130 mg, 2.0 mmol) was added. The mixture was stirred at 50° C. for 40 min, and then cooled to room temperature, poured into ice water, and extracted with DCM for 4 times. The combined extracts were washed with 10% LiCl, dried over MgSO₄, concentrated, and purified by flash chromatography using an ISCO system (Isco, Inc., Lincoln, Nebr.) with a 40 g column, Flow rate: 30 mL/min, solvent A: Hexane, solvent B: EtOAc. Gradient: 0% B to 60% B in 25 minutes to give racemic Examples 39i (89.6 mg, 34%) and 39ii (123.5 mg, 46%) both as white solids.

Example 39i: RT=2.492 min (Chromolith SpeedROD 4.6× 50 mm eluting with 10-90% aqueous methanol over 4 minutes containing 0.1% TFA, 4 mL/min, monitoring at 220 nm). MS (ES): m/z 458 [M+OAc]⁻.

Example 39ii: RT=2.611 min (Chromolith SpeedROD 4.6×50 mm eluting with 10-90% aqueous methanol over 4 minutes containing 0.1% TFA, 4 mL/min, monitoring at 220 nm). MS (ES): m/z 458 [M+OAc]⁻.

Examples 40i and 40ii methyl((1S,2R,6R,7S,8S)-4-(4-cyano-3-(trifluoromethyl)phenyl)-3,3-dioxido-10-oxa-3-thia-4-azatricyclo[5.2.1.0²,⁶]dec-8-yl)carbamate (40i) and methyl((1R,2S,6S,7R,8R)-4-(4-cyano-3-(trifluoromethyl)phenyl)-3,3-dioxido-10-oxa-3-thia-4-azatricyclo[5.2.1.0²,⁶]dec-8-yl)carbamate (40ii)

(40i)

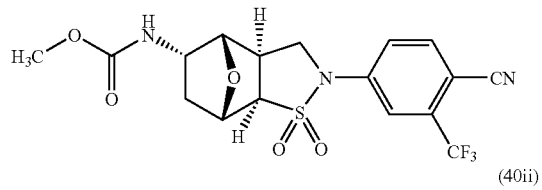

(40ii)

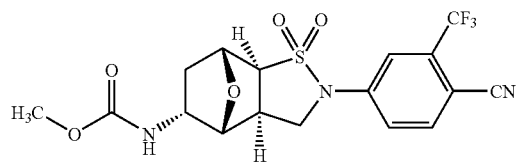

The racemic mixture of Example 40i and Example 40ii was prepared from Example 39i by the general method described in Examples 25 and 26.

The racemic mixture was separated into individual antipodes by use a Chiralpack AD 250×4.6 mm, 10 μm), flow rate: 1.0 mL/min, detector wavelength: 220 nm. Mobil phase hexanes/MeOH/DEA=5:95:0.1.

Example 40i: Chiral HPLC retention time=4.80 min, HPLC RT=2.270 min (Chromolith SpeedROD 4.6×50 mm eluting with 10-90% aqueous methanol over 4 minutes containing 0.1% TFA, 4 mL/min, monitoring at 220 nm). MS (ES): m/z 430 [M–H]⁻.

Example 40ii: Chiral HPLC retention time=12.9 min, HPLC RT=2.270 min (Chromolith SpeedROD 4.6×50 mm eluting with 10-90% aqueous methanol over 4 minutes containing 0.1% TFA, 4 mL/min, monitoring at 220 nm). MS (ES): m/z 430 [M–H]⁻.

Examples 41i and 41ii methyl((1S,2R,6R,7R,9R)-4-(4-cyano-3-(trifluoromethyl)phenyl)-3,3-dioxido-10-oxa-3-thia-4-azatricyclo[5.2.1.0²,⁶]dec-9-yl)carbamate (41i) and methyl((1R,2S,6S,7S,9S)-4-(4-cyano-3-(trifluoromethyl)phenyl)-3,3-dioxido-10-oxa-3-thia-4-azatricyclo[5.2.1.0²,⁶]dec-9-yl)carbamate (41ii)

(41i)

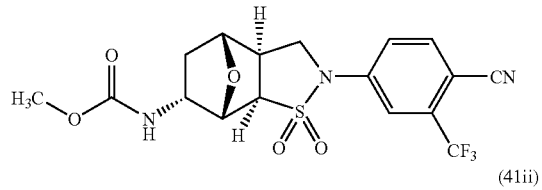

(41ii)

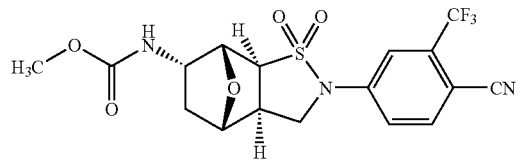

The racemic mixture of Example 41i and Example 41ii was prepared from Example 39ii by the general method described in Examples 25 and 26.

The racemic mixture was separated into individual antipodes by use a Chiralpack AD 250×4.6 mm, 10 μm), flow rate: 1.0 mL/min, detector wavelength: 220 nm. Mobil phase hexanes/MeOH/DEA=30:70:0.1.

Example 41i: Chiral HPLC retention time=5.5 min, HPLC RT=2.308 min (Chromolith SpeedROD 4.6×50 mm eluting with 10-90% aqueous methanol over 4 minutes containing 0.1% TFA, 4 mL/min, monitoring at 220 nm). MS (ES): m/z 430 [M−H]⁻.

Example 41ii: Chiral HPLC retention time=7.6 min, HPLC RT=2.308 min (Chromolith SpeedROD 4.6×50 mm eluting with 10-90% aqueous methanol over 4 minutes containing 0.1% TFA, 4 mL/min, monitoring at 220 nm). MS (ES): m/z 430 [M−H]⁻.

Example 42 rac-benzyl (1S,2S,6R,7S)-4-(4-cyano-3-(trifluoromethyl)phenyl)-3-thia-4,8-diazatricyclo[5.2.2.0$^{2,6}$] undec-10-ene-8-carboxylate 3,3-dioxide

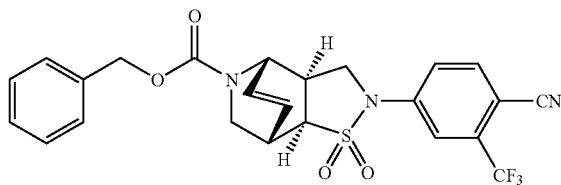

Step A: Benzyl pyridine-1(2H)-carboxylate

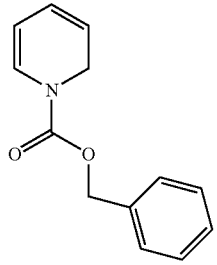
(42A)

Pyridine (5.0 mL, 61.8 mmol) was dissolved in EtOH (30 mL) and benzylchloroformate (8.86 mL, 61.8 mmol) was added. The mixture was cooled to −78° C. and NaBH₄ (2.58 g, 67.9 mmol) was added. After 2 hours at −78° C., the reaction mixture was quenched by pouring into crushed ice. This mixture was extracted with methylene chloride (3×100 mL). The combined organic extracts were washed once with 1 N HCl (50 mL) and dried over Na₂SO₄ to afford 7.78 g of Compound 42A as a white solid.

Step B: rac-benzyl (1S,2S,6S,7S)-4-(4-cyano-3-(trifluoromethyl)phenyl)-5-oxo-3-thia-4,8-diazatricyclo [5.2.2.0$^{2,6}$]undec-10-ene-8-carboxylate 3,3-dioxide

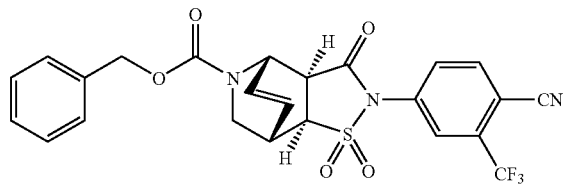 [SMILES: N#Cc1ccc(N2C[C@H]3[C@H]([C@H]4C=C[C@@H]3N(C(=O)OCc3ccccc3)C4)S2(=O)=O)cc1C(F)(F)F]
(42B)

Compound 42A (0.802 g, 3.73 mmol) was dissolved in THF (3.0 mL) and Compound 1D (1.0 g, 2.49 mmol) was added with stirring. The mixture was heated to 50° C. for 1 hour, and then cooled to 22° C. and concentrated in vacuo to give a orange solid. The crude material was purified by flash chromatography on silica eluting with 0-5% acetone in chloroform to give 1.52 g of Compound 42B as a white solid. NMR showed only one diastereomer and regioisomer to be present.

73% at 3.496 min (retention time) (YMC ODS-A column 4 6×50 mm eluting with 10-90% aqueous methanol over 4 minutes containing 0.1% H₃PO₄, 4 mL/min, monitoring at 220 nm).

Step C: rac-benzyl (1S,4S,7S,8S)-8-(((4-cyano-3-(trifluoromethyl)phenyl)amino) sulfonyl)-7-(hydroxymethyl)-2-azabicyclo[2.2.2]oct-5-ene-2-carboxylate

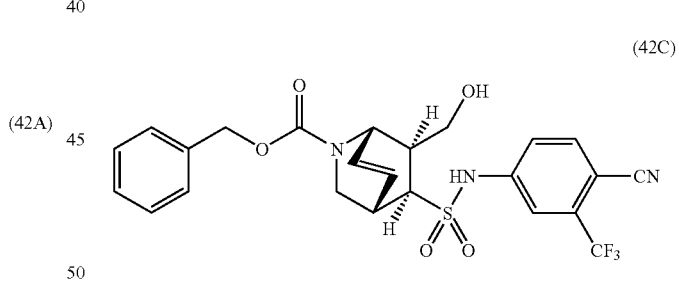
(42C)

Compound 42B (1.38 g, 2.67 mmol) was dissolved in THF (40 mL) and MeOH (2.0 mL) was added followed by cooling to 0° C. NaBH₄ (0.253 g, 6.67 mmol) was then added resulting in vigorous bubbling. The reaction mixture was warmed to 22° C. and stirred for 2 hours at which time it was quenched with saturated aqueous NH₄Cl and extracted with EtOAc (2×50 mL). The combined organic extracts were washed with brine and dried over anhydrous MgSO₄, and then concentrated in vacuo to afford Compound 42C as a yellow solid (1.27 g).

86% at 3.341 min (retention time) (YMC ODS-A column 4 6×50 mm eluting with 10-90% aqueous methanol over 4 minutes containing 0.1% H₃PO₄, 4 mL/min, monitoring at 220 nm).

Example 42

Compound 42C (1.21 g, 2.32 mmol) was dissolved in dry THF (30 mL) and Ph$_3$P (0.904 g, 3.48 mmol) was added followed by DIAD (0.683 mL, 3.48 mmol). After 1 hour, the reaction was complete as measured by HPLC and was concentrated in vacuo to give a yellow solid. The solid was purified by flash chromatography on silica gel eluting with 0-5% acetone in CH$_2$Cl$_2$ to give 1.09 g of racemic Example 42 as a white foam.

98% at 3.495 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 562.2 [M−H+OAc]$^-$.

Example 43 rac-benzyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide

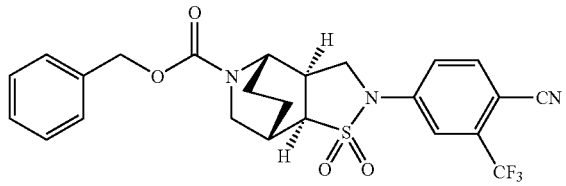 [SMILES: N#Cc1ccc(N2C[C@H]3[C@H]([C@H]4CC[C@@H]3N(C(=O)OCc3ccccc3)C4)S2(=O)=O)cc1C(F)(F)F]

Example 1 (0.500 g, 0.99 mmol) was dissolved in EtOAc and 10% Pd/C (0.10 g) was added followed by introduction of hydrogen via a balloon. After 1.5 hours, the reaction mixture was purged with nitrogen and filtered thru celite and rinsed with EtOAc. The filtrate was concentrated in vacuo to afford racemic Example 43 (0.498 g) as a white foam.

99% at 3.505 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 564.3 [M−H+OAc]$^-$.

Example 44 rac-4-((1R,2R,6S,7R)-3,3-dioxido-3-thia-4,8-diazatricyclo[5.2.2.0$^{2,6}$]undec-4-yl)-2-(trifluoromethyl)benzonitrile

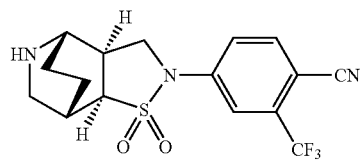

Example 1 (0.500 g, 0.99 mmol) was dissolved in MeOH and 10% Pd/C (DeGussa Type wet, 0.10 g) was added followed by the introduction of hydrogen via a balloon. After 1.5 hours, the reaction mixture was purged with nitrogen and filtered thru celite and rinsed with EtOAc. The filtrate was concentrated in vacuo to afford racemic Example 44 (0.412 g) as a white foam.

99% at 2.053 min (retention time) (YMC ODS-A column 4 6×50 mm eluting with 10-90% aqueous methanol over 4 minutes containing 0.1% H$_3$PO$_4$, 4 mL/min, monitoring at 220 nm). MS (ES): m/z 430.2 [M−H+OAc]$^-$.

Example 45 rac-4-((1R,2R,6S,7R)-8-acetyl-3,3-dioxido-3-thia-4,8-diazatricyclo[5.2.2.02,6]undec-4-yl)-2-(trifluoromethyl)benzonitrile

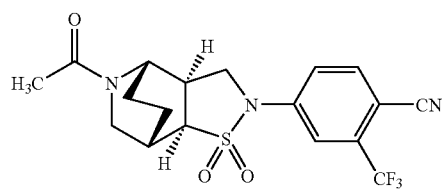 [SMILES: CC(=O)N1C[C@@H]2CC[C@H]1[C@H]1CN(c3ccc(C#N)c(C(F)(F)F)c3)S(=O)(=O)[C@@H]21]

Example 3 (0.040 g, 0.11 mmol) was dissolved in CH$_2$Cl$_2$ (1.0 mL) followed by addition of DIEA (0.038 mL, 0.22 mmol) and acetyl chloride (0.012 mL, 0.17 mmol). After 1 hour, the reaction mixture was diluted with CH$_2$Cl$_2$ and washed once with 1 N HCl (5 mL), once with saturated aqueous NaHCO$_3$ (5 mL) and then dried over Na$_2$SO$_4$. After concentration, racemic Example 45 (0.039 g) was afforded of as a white solid.

99% at 2.800 min (retention time) (YMC ODS-A column 4.6×50 mm eluting with 10-90% aqueous methanol over 4 minutes containing 0.1% H$_3$PO$_4$, 4 mL/min, monitoring at 220 nm). MS (ES): m/z 472.10 [M−H+OAc]$^-$.

Examples 46 to 48 rac-4-((1R,2R,6S,7R)-8-(ethylsulfonyl)-3,3-dioxido-3-thia-4,8-diazatricyclo[5.2.2.0$^{2,6}$]undec-4-yl)-2-(trifluoromethyl)benzonitrile (46)

methyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide (47) and phenyl rac-(1R,2R,6S,7R)-4-(4-cyano-3-(trifluoromethyl)phenyl)-3-thia-4,8-diazatricyclo[5.2.2.0$^{2,6}$]undecane-8-carboxylate 3,3-dioxide (48)

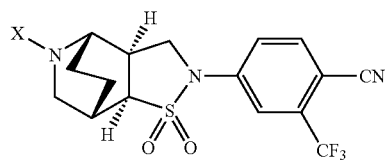

Compounds having the formulae above, wherein the group X has the values reported in Table 1, were prepared. The compounds of Table 1 were prepared by the general procedure described in Example 4, using Example 3 as a starting material, and then coupling an appropriate sulfonyl chloride or chloroformate, applying standard amine-coupling techniques known in the field and/or as described above in Examples 4 and/or as otherwise described herein. All compounds shown are racemic.

TABLE 1

| Example No. | X | Retention Time Min./Molecular Mass |
|---|---|---|
| 46 | -S(=O)₂-CH₃ group | 2.933 LCMS [M − H + OAc]⁻ = 522.07 |
| 47 | -O-C(=O)-CH₃ group | 3.095 LCMS [M − H + OAc]⁻ = 488.06 |
| 48 | -C(=O)-O-phenyl group | 3.350 LCMS [M − H + OAc]⁻ = 550.4 |

Biological Testing of Compounds

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, are incubated at 37° C. to remove any endogenous ligand that might be complexed with the receptor in the cells. After 48 hours, either a saturation analysis to determine the $K_d$ for tritiated dihydrotestosterone, [³H]-DHT, or a competitive binding assay to evaluate the ability of test compounds to compete with [³H]-DHT is performed. For the saturation analysis, media (RPMI 1640 or DMEM-0.2% CA-FBS) containing [³H]-DHT (in concentrations ranging from 0.1 nM to 16 nM) in the absence (total binding) or presence (non-specific binding) of a 500-fold molar excess of unlabeled DHT are added to the cells. After 4 hours at 37° C., an aliquot of the total binding media at each concentration of [³H]-DHT is removed to estimate the amount of free [³H]-DHT. The remaining media is removed, cells are washed three times with PBS and harvested onto UniFilter GF/B plates (Packard), Microscint (Packard) is added and plates counted in a Top-Counter (Packard) to evaluate the amount of bound [³H]-DHT.

For the saturation analysis, the difference between the total binding and the non-specific binding is defined as specific binding. The specific binding is evaluated by Scatchard analysis to determine the $K_d$ for [³H]-DHT. See e.g., D. Rodbard, *Mathematics and Statistics of Ligand Assays: An Illustrated Guide*: In: J. Langon and J. J. Clapp, eds., *Ligand Assay*, Masson Publishing U.S.A., Inc., New York, pp. 45-99 (1981), the disclosure of which is herein incorporated by reference.

For the competition studies, media containing 2 nM [³H]-DHT and compounds of the invention ("test compounds") in concentrations ranging from $10^{-10}$ to $10^{-5}$ M are added to the cells. Two replicates are used for each sample. After 90 min at 37° C., cells are washed, harvested, and counted as described above. The data is plotted as the amount of [³H]-DHT (% of control in the absence of test compound) remaining over the range of the dose response curve for a given compound. The concentration of test compound that inhibited 50% of the amount of [³H]-DHT bound in the absence of competing ligand is quantified ($IC_{50}$) after log-logit transformation. The $K_i$ values are determined by application of the Cheng-Prusoff equation to the $IC_{50}$ values, where:

$$K_i = \frac{IC_{50}}{(1 + [^3H\text{-}DHT]/K_d \text{ for } ^3H\text{-}DHT)}.$$

After correcting for non-specific binding, $IC_{50}$ values are determined. The $IC_{50}$ is defined as the concentration of competing ligand needed to reduce specific binding by 50%. The $K_d$ values for [³H]-DHT for MDA 453 is 0.7 nM.

Compounds described herein, e.g., in the examples, were tested and found to show affinity to the androgen receptor.

AR Binding Assay

For the whole cell binding assay, human breast adenocarcinoma MDA-MB-453 cells (American Type Culture Collection, Rockville, Md., ATCC #: HTB-131), expressing a functional endogenous wild type AR, are grown to near confluency in T-225 tissue culture flasks containing Dulbecco's Modified Eagle Medium (DMEM) (Mediatech CAT #45000-668) supplemented with 10% fetal bovine serum (FBS) (Invitrogen/GIBCO Life Science). In order to remove any endogenous ligand that might be complexed with the receptor in the cells, the tissue culture media is removed and the cells are incubated overnight at 37° C. in serum-free DMEM. The next day, cells are rinsed with magnesium and calcium free Phosphate Buffered Saline (PBS) (Invitrogen/GIBCO Life Science), harvested using Cell Stripper Buffer (Mediatech) and re-suspended in serum-free DMEM to achieve a final assay concentration of $4 \times 10^5$ cells/well of a 96-well assay plate. Saturation analysis or competitive binding assays with tritiated dihydrotestosterone ([³H]-DHT) are used to evaluate $K_d$ and $K_i$ values of the test compounds, respectively. For the saturation analysis, media (DMEM-10% charcoal stripped CA-FBS, Hyclone) containing [³H]-DHT (in concentrations ranging from 0.1 nM to 16 nM) in the absence (total binding) or presence (non-specific binding) of a 500-fold molar excess of unlabeled DHT are added to the cells. After 90 minutes at room temperature, an aliquot of the total binding media at each concentration of [³H]-DHT is removed to estimate the amount of free [³H]-DHT. After the remaining media is removed, cells are washed three times with PBS and harvested onto UniFilter GF/B plates (PerkinElmer). Microscint 20 solution (PerkinElmer) is added and the plates are counted on a TopCount detector (Packard) to evaluate the amount of bound [³H]-DHT. The specific binding is evaluated by Scatchard analysis to determine the $K_d$ for [³H]-DHT.

For the competition studies, media containing 2 nM [³H]-DHT and test compounds in concentrations ranging from $10^{-10}$ to $10^{-5}$ M are added to the cells. Two replicates are used for each sample. After 90 minutes at room temperature, cells are harvested by filtering through a GF/B filter plate (PerkinElmer) followed by washing with ice-cold 1×PBS (without calcium and magnesium) to remove unbound label. The competition data of the test compounds over the range of concentrations is plotted as percentage inhibition of [³H]-DHT specific bound in the absence of test compounds (percent of total signal). After correcting for non-specific binding, $IC_{50}$ values are determined. The $IC_{50}$ value is defined as the concentration of competing ligand needed to reduce specific binding by 50%. The concentration of test compound that inhibited 50% of the amount of [³H]-DHT specific bound ($IC_{50}$) is quantified using the four parameter logistic equation to fit the data.

The $K_i$ values are determined by application of the Cheng-Prusoff equation to the $IC_{50}$ values where:

$$K_I = \frac{IC_{50}}{(1 + [^3H\text{-}DHT]/K_d \text{ for } ^3H\text{-}DHT)}.$$

The $K_d$ for [$^3$H]-DHT for MDA-MB-453 was 0.4 nM.

The specific binding is evaluated by Scatchard analysis to determine the $K_d$ for [$^3$H]-DHT. See e.g., D. Rodbard, *Mathematics and Statistics of Ligand Assays: An Illustrated Guide*: In: J. Langon and J. J. Clapp, eds., *Ligand Assay*, Masson Publishing U.S.A., Inc., New York, pp. 45-99 (1981).

Compounds described herein were tested in the AR Binding Assay described immediately above. The following results were obtained.

TABLE 2

AR Binding Assay

| Example | $K_I$ (nM) |
|---|---|
| 1ii | 29 |
| 4 | 221 |
| 6 | 23 |
| 9 | 92 |
| 10ii | 745 |
| 10iii | 568 |
| 14 | 11 |
| 18 | 222 |
| 21i | 173 |
| 21ii | 145 |
| 26i | 266 |
| 37i | 10 |
| 38ii | 10 |
| 40i | 46 |
| 41i | 354 |

Androgen Receptor Transactivation Assay using MDA-MB-453 or 22 RV1 Cell Lines

Compounds can be tested in a cell based transactivation assay used to measure the antagonism of androgen receptor (AR) transcriptional activity. The transactivation assay provides a means of identifying antagonists that inhibit the effects of the native hormone dihydrotestosterone (DHT). The human breast adenocarcinoma MDA-MB-453 cell line (American Type Culture Collection, Rockville, Md., ATCC#: HTB-131), expressing a functional endogenous wild type AR, was transiently transfected with a reporter plasmid and tested for AR dependent transactivation activity in the absence or presence of test compounds. The pGL3 PSA-Luc reporter plasmid is comprised of the cDNA for the firefly luciferase gene and the upstream promoter sequences containing the androgen response elements (AREs) of the prostate specific antigen (PSA). This plasmid functions as a reporter for the transcription-modulating activity of the AR. In order to detect antagonists, the transactivation assay is conducted in the presence of constant concentration of the natural AR hormone (DHT) to induce a defined reporter signal. Addition of increasing concentrations of the suspected antagonist will decrease the reporter signal (luciferase activity).

MDA-MB-453 and 22 RV1 cells were maintained in DMEM (Cellgro, Cat. #10-014-CM) or RPMI 1640 (Gibco Cat. #11875-085) respectively and supplemented with 10% FBS (Invitrogen/GIBCO Life Science). Cells were bulk transfected in flasks with 1.3 ug/ml pGL3 PSA-Luc plasmid by using the Lipofectamine 2000 Reagent (Invitrogen, Cat. #11668-019) and serum-free Opti-MEM I media (Invitrogen, Cat#31985-070) according to the manufacturer's optimized conditions. Transfection was conducted at 37° C. with 5% $CO_2$ for 16-18 hours. Following transfection, cells are washed, treated with trypsin, counted, and seeded in a 96-well plate at 30,000 cells per well in DMEM containing 10% Charcoal/Dextran Treated Fetal Bovine Serum (Gibco Cat. #11054-020) for MDA-MB-453 cells or RPMI 1640 (Gibco Cat. #110835) containing 10% FBS (Invitrogen/GIBCO Life Science) for 22 RV1 cells.

Following transfection, cells were incubated in the absence (blank) or presence (control) of 3 nM DHT (Sigma, Cat. #A-8380) and in the presence or absence of the standard antiandrogen bicalutamide or test compounds ranging in concentrations from $10^{-10}$ to $10^{-5}$M. Duplicates were used for each sample. The compound dilutions were performed by the Tecan Genesis (Tecan, Triangle Park, N.C.). After a 48 hour incubation, luciferase activity was measured using the Steady-Glo Luciferase Assay System (Promega, Cat. #E2550) according to manufacturer's specifications and luminescence was measured on a Packard TopCount (Perki-nElmer). For each luciferase sample reading, the percent control (in absence of compounds) was calculated as:

% Control=100×[average$_{sample}$−average$_{blank}$]/[average$_{control}$−average$_{blank}$]

Data was plotted and the $IC_{50}$ value was defined as the concentration of compound that inhibited 50% of the luciferase activity for the controls.

Compounds described herein were tested in the AR transactivation assay described immediately above, using MDA-MB-453 cells. The following results were obtained.

TABLE 3

MDA-MB-453 Androgen Receptor Transactivation Assay

| Example | $IC_{50}$ (nM) |
|---|---|
| 1ii | 108 |
| 4 | 1420 |
| 6 | 198 |
| 9 | 2640 |
| 10ii | 7500 |
| 10iii | 8320 |
| 14 | 144 |
| 18 | 1350 |
| 21i | 1160 |
| 21ii | 1110 |
| 26i | 3130 |
| 37i | 154 |
| 38ii | 141 |
| 40i | 977 |
| 41i | 8250 |

Immature Rat Prostate Weight (IRPW) Assay

The activity of compounds of Formula (I) as AR antagonists can be investigated in an immature male rat model, as described in L. G. Hershberger et al., *Proc. Soc. Expt. Biol. Med.*, 83:175 (1953); P. C. Walsh and R. F. Gittes, "Inhibition of extratesticular stimuli to prostate growth in the castrated rat by antiandrogens", *Endocrinology*, 86:624 (1970); and B. J. Furr et al., "ICI 176,334: A novel non-steroid, peripherally selective antiandrogen", *J. Endocrinol.*, 113, R7-9 (1987), the disclosures of which are herein incorporated by reference.

Male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al., *Clin. Invest. Med.*, 16:475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, *The Physiology of Reproduction*, E. Knobil and J. D. Neill, eds. 1:1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawley) are castrated under metofane anesthesia. Five days after surgery these castrated rats (60-70g, 23-25 day-old) are dosed for 3 days Animals are dosed sub-cutaneously (s.c.) 1 mg/kg with Testosterone Proprionate (TP) in arachis oil vehicle and anti-androgen test compounds (compounds of formula (I)) are dosed orally by gavage (p.o.) in dissolved/suspensions of 80% PEG 400 and 20% Tween 80 surfactant(PEGTW). Animals are dosed (v/w) at 0.5 ml of vehicle/100g body weight. Experimental groups are as follows:

1. Control vehicle
2. Testosterone Propionate (TP) (3 mg/rat/day, subcutaneous)
3. TP plus bicalutamide (administered p.o. in PEGTW, QD), a recognized antiandrogen, as a reference compound.
4. To demonstrate antagonist activity, a compound of formula (I) ("test compound") is administered (p.o. in PEGTW, QD) with TP (s.c. as administered in group 2) in a range of doses.
5. To demonstrate agonist activity a compound of formula (I) ("test compound") is administered alone (p.o. in PEGTW, QD) in a range of doses.

At the end of the 3-day treatment, the animals are sacrificed, and the ventral prostate weighed. To compare data from different experiments, the sexual organs weights are first standardized as mg per 100 g of body weight, and the increase in organ weight induced by TP was considered as the maximum increase (100%). ANOVA followed by one-tailed Student or Fischer's exact test is used for statistical analysis.

The gain and loss of sexual organ weight reflect the changes of the cell number (DNA content) and cell mass (protein content), depending upon the serum androgen concentration. See Y. Okuda et al., *J. Urol.*, 145:188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP showed about 10-30-fold higher potency than free T.

[$^3$H]-Thymidine Incorporation

Flag-AR-LNCaP cells are derived from prostate cancer LnCap cells with a wild-type AR fused with a Flag tag stable transfected into parental LnCap cells. These cells with increased AR level confer resistance to antiandrogens. Flag-AR-LnCap cells are maintained in RPMI medium with 10% serum and 800 ug/ml G418 for selection. In [$^3$H]-Thymidine Incorporation assays, LnCap or Flag-AR-LnCap cells are seeded at 6000 cells/well in 96 well plates and maintained in phenol red-free RPMI medium supplemented with 5% charcoal dextran-stripped serum. After 24 hours, compounds are added to the cells in the presence of final concentration of 0.5 nM DHT. Four days after the compound treatment, [$^3$H]-thymidine pulsing for 4 hours is followed by plate harvesting and counting using TOPCOUNT detector.

For each replicate, the % Inhibition (compared to controls in the absence of compounds) is calculated as: %

$$\text{Inhibition}=100\times[1-[[\text{average}_{sample}-\text{average}_{blank}]/[\text{average}_{control}-\text{average}_{blank}]]]$$

Data is plotted and the $IC_{50}$ is defined as the concentration of compound that exhibited an inhibition of 50% of the [$^3$H]-thymidine incorporation observed in the controls in the absence of compounds.

Human Tumor Xenograft Assay

Three human tumor xenografts are utilized: CWR-22 (Wainstein et al., 1994), LuCap 23.1 (Ellis et al., 1996), and LuCap 35 (Linja et al., 2001). The CWR-22 line was obtained from Dr. T. Prestlow (Case Western Reserve), and the LuCap 23.1 and LuCap 35 lines were received from Dr. Robert Vesella (University of Washington, Seattle, Wash.).

The tumor lines are maintained in Balb/c athymic (nu/nu) mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approximately 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2-Wt_1$) provides a measure of treatment-related toxicity.

Tumors are measured weekly for the LuCap 23.1 and LuCap 35 studies, and twice weekly for the CWR-22 studies. Tumor size ($mm^3$) is calculated from the formula: Tumor weight=(length×width)÷2. Body weights are obtained weekly.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

$TVDT$=[(Median time (days) for control tumors to reach target size)−(Median time (days) for control tumors to reach half the target size)]. And, Log cell kill=$(T-C)\div(3.32\times TVDT)$ Statistical evaluations of data are performed using Gehan's generalized Wilcoxon test.

What is claimed is:

1. A compound which is:
rac-4-((1R,2R,6R,7S)-3,3-dioxido-10-oxa-3-thia-4-azatricyclo[5.2.1.0$^{2,6}$]dec-8-en-4-yl)-2-(trifluoromethyl) benzonitrile (1i);
rac-4-((1R,2S,6S,7S)-3,3-dioxido-10-oxa-3-thia-4-azatricyclo[5.2.1.0$^{2,6}$]dec-8-en-4-yl)-2-(trifluoromethyl) benzonitrile (1ii);
4-((1S,2S,6S,7R)-3,3-dioxido-10-oxa-3-thia-4-azatricyclo[5.2.1.0$^{2,6}$]dec-8-en-4-yl)-2-(trifluoromethyl)benzonitrile (2i);
4-((1R,2R,6R,7S)-3,3-dioxido-10-oxa-3-thia-4-azatricyclo[5.2.1.0$^{2,6}$]dec-8-en-4-yl)-2-(trifluoromethyl)benzonitrile (2ii);
4-((1S,2S,6S,7R)-2-methyl-3,3-dioxido-10-oxa-3-thia-4-azatricyclo[5.2.1.0$^{2,6}$]dec-8-en-4-yl)-2-(trifluoromethyl)benzonitrile (3);
4-((1R,2R,6R,7S)-2-methyl-3,3-dioxido-10-oxa-3-thia-4-azatricyclo[5.2.1.0$^{2,6}$]dec-8-en-4-yl)-2-(trifluoromethyl)benzonitrile (4);
4-((1S,2R,6R,7R)-3,3-dioxido-10-oxa-3-thia-4-azatricyclo[5.2.1.0$^{2,6}$]dec-8-en-4-yl)-2-(trifluoromethyl)benzonitrile (5i);
4-((1R,2S,6S,7S)-3,3-dioxido-10-oxa-3-thia-4-azatricyclo[5.2.1.0$^{2,6}$]dec-8-en-4-yl)-2-(trifluoromethyl)benzonitrile (5ii);
4-((1S,2R,6R,7S,8S,10S)-3,3-dioxido-9,11-dioxa-3-thia-4-azatetracyclo[5.3.1.0$^{2,6}$.0$^{8,10}$]undec-4-yl)-2-(trifluoromethyl)benzonitrile (8);
4-((1R,2S,6S,7R,8R,10R)-3,3-dioxido-9,11-dioxa-3-thia-4-azatetracyclo[5.3.1.0$^{2,6}$.0$^{8,10}$]undec-4-yl)-2-(trifluoromethyl)benzonitrile (9);
rac-4-((1R,2R,6R,7S,9R)-9-hydroxy-3,3-dioxido-10-oxa-3-thia-4-azatricyclo[5.2.1.0$^{2,6}$]dec-4-yl)-2-(trifluoromethyl)benzonitrile (10i);
rac-4-((1R,2R,6R,7R,8S)-8-hydroxy-3,3-dioxido-10-oxa-3-thia-4-azatricyclo[5.2.1.0$^{2,6}$]dec-4-yl)-2-(trifluoromethyl)benzonitrile (10ii);
rac-4-((1R,2R,6R,7R,8R)-8-hydroxy-3,3-dioxido-10-oxa-3-thia-4-azatricyclo[5.2.1.0$^{2,6}$]dec-4-yl)-2-(trifluoromethyl)benzonitrile (10iii);
4-((1S,2R,6R,7R,9S)-9-hydroxy-3,3-dioxido-10-oxa-3-thia-4-azatricyclo[5.2.1.0$^{2,6}$]dec-4-yl)-2-(trifluoromethyl)benzonitrile (13);
4-((1S,2R,6R,7R,9R)-9-fluoro-3,3-dioxido-10-oxa-3-thia-4-azatricyclo[5.2.1.0$^{2,6}$]dec-4-yl)-2-(trifluoromethyl)benzonitrile (14);
4-((1R,2S,6S,7S,9R)-9-hydroxy-3,3-dioxido-10-oxa-3-thia-4-azatricyclo[5.2.1.0$^{2,6}$]dec-4-yl)-2-(trifluoromethyl)benzonitrile (15);
4-((1R,2S,6S,7S,9S)-9-fluoro-3,3-dioxido-10-oxa-3-thia-4-azatricyclo[5.2.1.0$^{2,6}$]dec-4-yl)-2-(trifluoromethyl)benzonitrile (16);
rac-4-((1R,2R,6R,7S)-1,7-dimethyl-3,3-dioxido-10-oxa-3-thia-4-azatricyclo[5.2.1.0$^{2,6}$]dec-8-en-4-yl)-2-(trifluoromethyl)benzonitrile (17);
rac-4-((1S,2S,6R,7R)-1,7-dimethyl-3,3-dioxido-10-oxa-3-thia-4-azatricyclo[5.2.1.0$^{2,6}$]dec-8-en-4-yl)-2-(trifluoromethyl)benzonitrile (17A);
rac-4-((1R,2R,6R,7S)-1,7-dimethyl-3,3-dioxido-10-oxa-3-thia-4-azatricyclo[5.2.1.0$^{2,6}$]dec-4-yl)-2-(trifluoromethyl)benzonitrile (18);
rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (19);
rac-4-((1S,2R,6S,7R)-7-methyl-3,3-dioxido-5-oxo-10-oxa-3-thia-4-azatricyclo[5.2.1.0$^{2,6}$]dec-8-en-4-yl)-2-(trifluoromethyl)benzonitrile (19A);
rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (20);
rac-4-((1R,2R,6R,7S)-7-methyl-3,3-dioxido-10-oxa-3-thia-4-azatricyclo[5.2.1.0$^{2,6}$]dec-8-en-4-yl)-2-(trifluoromethyl)benzonitrile (21i);
rac-4-((1R,2R,6R,7S)-1-methyl-3,3-dioxido-10-oxa-3-thia-4-azatricyclo[5.2.1.0$^{2,6}$]dec-8-en-4-yl)-2-(trifluoromethyl)benzonitrile (21ii);
rac-4-((1S,2S,6R,7R)-7-methyl-3,3-dioxido-5-oxo-10-oxa-3-thia-4-azatricyclo[5.2.1.0$^{2,6}$]dec-8-en-4-yl)-2-(trifluoromethyl)benzonitrile (21A)
rac-4-((1R,2R,6R,7S)-7-methyl-3,3-dioxido-10-oxa-3-thia-4-azatricyclo[5.2.1.0$^{2,6}$]dec-4-yl)-2-(trifluoromethyl)benzonitrile (22);
rac-4-((1R,2R,6R,7S)-1-methyl-3,3-dioxido-10-oxa-3-thia-4-azatricyclo[5.2.1.0$^{2,6}$]dec-4-yl)-2-(trifluoromethyl)benzonitrile (23);
rac-4-((1R,2R,6R,7R,8S)-8-azido-3,3-dioxido-10-oxa-3-thia-4-azatricyclo[5.2.1.0$^{2,6}$]dec-4-yl)-2-(trifluoromethyl)benzonitrile (24i);
rac-4-((1R,2R,6R,7S,9R)-9-azido-3,3-dioxido-10-oxa-3-thia-4-azatricyclo[5.2.1.0$^{2,6}$]dec-4-yl)-2-(trifluoromethyl)benzonitrile (24ii);
rac-4-((1R,2R,6R,7R,8S)-8-amino-3,3-dioxido-10-oxa-3-thia-4-azatricyclo[5.2.1.0$^{2,6}$]dec-4-yl)-2-(trifluoromethyl)benzonitrile (25i);
rac-4-((1R,2R,6R,7S,9R)-9-amino-3,3-dioxido-10-oxa-3-thia-4-azatricyclo[5.2.1.0$^{2,6}$]dec-4-yl)-2-(trifluoromethyl)benzonitrile (25ii);
methyl rac-((1R,2R,6R,7R,8S)-4-(4-cyano-3-(trifluoromethyl)phenyl)-3,3-dioxido-10-oxa-3-thia-4-azatricyclo[5.2.1.0$^{2,6}$]dec-8-yl)carbamate (26i);
methyl rac-((1R,2R,6R,7S,9R)-4-(4-cyano-3-(trifluoromethyl)phenyl)-3,3-dioxido-10-oxa-3-thia-4-azatricyclo[5.2.1.0$^{2,6}$]dec-9-yl)carbamate (26ii);
benzyl (1S,2S,6S,7R)-4-(4-cyano-3-(trifluoromethyl)phenyl)-10-oxa-3-thia-4-azatricyclo[5.2.1.0$^{2,6}$]decane-2-carboxylate 3,3-dioxide (27);
(1S,2S,6S,7R)-4-(4-cyano-3-(trifluoromethyl)phenyl)-10-oxa-3-thia-4-azatricyclo[5.2.1.0$^{2,6}$]decane-2-carboxylic acid 3,3-dioxide (28);
(1S,2S,6S,7R)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (29);
benzyl (1R,2R,6R,7S)-4-(4-cyano-3-(trifluoromethyl)phenyl)-10-oxa-3-thia-4-azatricyclo[5.2.1.0$^{2,6}$]decane-2-carboxylate 3,3-dioxide (30);
(1R,2R,6R,7S)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (31);
rac-(1R,2S,6S,7S)-4-(4-cyano-3-(trifluoromethyl)phenyl)-N-methyl-10-oxa-3-thia-4-azatricyclo[5.2.1.0$^{2,6}$]decane-2-carboxamide 3,3-dioxide (33);
rac-4-((1R,2S,6S,7R,8S)-8-hydroxy-3,3-dioxido-10-oxa-3-thia-4-azatricyclo[5.2.1.0$^{2,6}$]dec-4-yl)-2-(trifluoromethyl)benzonitrile (34i);
rac-4-((1R,2S,6S,7R,9R)-9-hydroxy-3,3-dioxido-10-oxa-3-thia-4-azatricyclo[5.2.1.0$^{2,6}$]dec-4-yl)-2-(trifluoromethyl)benzonitrile (34ii);
rac-4-((1R,2S,6S,7R,8R)-8-hydroxy-3,3-dioxido-10-oxa-3-thia-4-azatricyclo[5.2.1.0$^{2,6}$]dec-4-yl)-2-(trifluoromethyl)benzonitrile (34iii);

rac-4-((1R,2S,6S,7S,9S)-9-hydroxy-3,3-dioxido-10-oxa-3-thia-4-azatricyclo[5.2.1.0²,⁶]dec-4-yl)-2-(trifluoromethyl)benzonitrile (34iv);

rac-4-((1R,2S,6S,7R,8R)-8-fluoro-3,3-dioxido-10-oxa-3-thia-4-azatricyclo[5.2.1.0²,⁶]dec-4-yl)-2-(trifluoromethyl)benzonitrile (35i);

rac-4-((1R,2S,6S,7S,9S)-9-fluoro-3,3-dioxido-10-oxa-3-thia-4-azatricyclo[5.2.1.0²,⁶]dec-4-yl)-2-(trifluoromethyl)benzonitrile (35ii);

4-((1S,2R,6R,7S,8S)-8-fluoro-3,3-dioxido-10-oxa-3-thia-4-azatricyclo[5.2.1.0²,⁶]dec-4-yl)-2-(trifluoromethyl)benzonitrile (36i);

4-((1R,2S,6S,7R,8R)-8-fluoro-3,3-dioxido-10-oxa-3-thia-4-azatricyclo[5.2.1.0²,⁶]dec-4-yl)-2-(trifluoromethyl)benzonitrile (36ii);

4-((1S,2R,6R,7S,8S)-8-hydroxy-3,3-dioxido-10-oxa-3-thia-4-azatricyclo[5.2.1.0²,⁶]dec-4-yl)-2-(trifluoromethyl)benzonitrile (37i);

4-((1R,2S,6S,7R,8R)-8-hydroxy-3,3-dioxido-10-oxa-3-thia-4-azatricyclo[5.2.1.0²,⁶]dec-4-yl)-2-(trifluoromethyl)benzonitrile (37ii);

4-((1S,2R,6R,7R,9R)-9-hydroxy-3,3-dioxido-10-oxa-3-thia-4-azatricyclo[5.2.1.0²,⁶]dec-4-yl)-2-(trifluoromethyl)benzonitrile (38i);

4-((1R,2S,6S,7S,9S)-9-hydroxy-3,3-dioxido-10-oxa-3-thia-4-azatricyclo[5.2.1.0²,⁶]dec-4-yl)-2-(trifluoromethyl)benzonitrile (38ii);

rac-4-((1R,2S,6S,7R,8R)-8-azido-3,3-dioxido-10-oxa-3-thia-4-azatricyclo[5.2.1.0²,⁶]dec-4-yl)-2-(trifluoromethyl)benzonitrile (39i);

rac-4-((1R,2S,6S,7S,9S)-9-azido-3,3-dioxido-10-oxa-3-thia-4-azatricyclo[5.2.1.0²,⁶]dec-4-yl)-2-(trifluoromethyl)benzonitrile (39ii);

methyl((1S,2R,6R,7S,8S)-4-(4-cyano-3-(trifluoromethyl)phenyl)-3,3-dioxido-10-oxa-3-thia-4-azatricyclo[5.2.1.0²,⁶]dec-8-yl)carbamate (40i);

methyl((1R,2S,6S,7R,8R)-4-(4-cyano-3-(trifluoromethyl)phenyl)-3,3-dioxido-10-oxa-3-thia-4-azatricyclo[5.2.1.0²,⁶]dec-8-yl)carbamate (40ii);

methyl((1S,2R,6R,7R,9R)-4-(4-cyano-3-(trifluoromethyl)phenyl)-3,3-dioxido-10-oxa-3-thia-4-azatricyclo[5.2.1.0²,⁶]dec-9-yl)carbamate (41i);

methyl((1R,2S,6S,7S,9S)-4-(4-cyano-3-(trifluoromethyl)phenyl)-3,3-dioxido-10-oxa-3-thia-4-azatricyclo[5.2.1.0²,⁶]dec-9-yl)carbamate (41ii);

rac-benzyl (1S,2S,6R,7S)-4-(4-cyano-3-(trifluoromethyl)phenyl)-3-thia-4,8-diazatricyclo[5.2.2.0²,⁶]undec-10-ene-8-carboxylate 3,3-dioxide (42);

rac-benzyl (1S,2S,6S,7S)-4-(4-cyano-3-(trifluoromethyl)phenyl)-5-oxo-3-thia-4,8-diazatricyclo[5.2.2.0²,⁶]undec-10-ene-8-carboxylate 3,3-dioxide (42B);

rac-benzyl rac-(1R,2R,6S,7R)-4-(4-cyano-3-(trifluoromethyl)phenyl)-3-thia-4,8-diazatricyclo[5.2.2.0²,⁶]undecane-8-carboxylate 3,3-dioxide (43);

rac-4-((1R,2R,6S,7R)-3,3-dioxido-3-thia-4,8-diazatricyclo[5.2.2.0²,⁶]undec-4-yl)-2-(trifluoromethyl)benzonitrile (44);

rac-4-((1R,2R,6S,7R)-8-acetyl-3,3-dioxido-3-thia-4,8-diazatricyclo[5.2.2.0²,⁶]undec-4-yl)-2-(trifluoromethyl)benzonitrile (45);

rac-4-((1R,2R,6S,7R)-8-(ethylsulfonyl)-3,3-dioxido-3-thia-4,8-diazatricyclo[5.2.2.0²,⁶]undec-4-yl)-2-(trifluoromethyl)benzonitrile (46);

methyl rac-(1R,2R,6S,7R)-4-(4-cyano-3-(trifluoromethyl)phenyl)-3-thia-4,8-diazatricyclo[5.2.2.0²,⁶]undecane-8-carboxylate 3,3-dioxide (47); or phenyl rac-(1R,2R,6S,7R)-4-(4-cyano-3-(trifluoromethyl)phenyl)-3-thia-4,8-diazatricyclo[5.2.2.0²,⁶]undecane-8-carboxylate 3,3-dioxide (48); or a pharmaceutically-acceptable salt or stereoisomer thereof.

2. A pharmaceutical composition comprising:
a) at least one compound according to claim 1 or a pharmaceutically-acceptable salt thereof;
b) at least one pharmaceutically-acceptable carrier and/or diluent; and
c) optionally, at least one other anti-cancer agent.

3. A compound having the structure

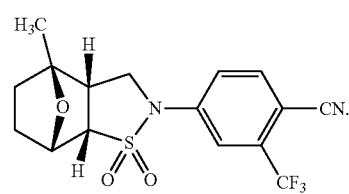

(22)

* * * * *